United States Patent
Leamon et al.

(10) Patent No.: US 9,549,992 B2
(45) Date of Patent: Jan. 24, 2017

(54) FOLATE RECEPTOR BINDING CONJUGATES OF ANTIFOLATES

(71) Applicants: Purdue Research Foundation, West Lafayette, IN (US); Endocyte, Inc., West Lafayette, IN (US)

(72) Inventors: Christopher Paul Leamon, West Lafayette, IN (US); Iontcho Radoslavov Vlahov, West Lafayette, IN (US); Philip Stewart Low, West Lafayette, IN (US)

(73) Assignees: Purdue Research Foundation, West Lafayette, IN (US); Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/919,518

(22) Filed: Oct. 21, 2015

(65) Prior Publication Data

US 2016/0263237 A1     Sep. 15, 2016

Related U.S. Application Data

(63) Continuation of application No. 14/010,122, filed on Aug. 26, 2013, now Pat. No. 9,192,682, which is a continuation of application No. 13/063,889, filed as application No. PCT/US2009/057363 on Sep. 17, 2009, now Pat. No. 8,546,525.

(60) Provisional application No. 61/097,655, filed on Sep. 17, 2008.

(51) Int. Cl.
| | | |
|---|---|---|
| *A01N 43/54* | (2006.01) | |
| *A61K 31/517* | (2006.01) | |
| *A61K 47/48* | (2006.01) | |
| *A61K 31/475* | (2006.01) | |

(52) U.S. Cl.
CPC ....... *A61K 47/48338* (2013.01); *A61K 31/475* (2013.01); *A61K 31/517* (2013.01); *A61K 47/48061* (2013.01)

(58) Field of Classification Search
None
See application file for complete search history.

(56) References Cited

U.S. PATENT DOCUMENTS

| 4,713,249 A | 12/1987 | Schroder |
| 5,266,333 A | 11/1993 | Cady et al. |
| 5,417,982 A | 5/1995 | Modi |
| 2004/0242582 A1 | 12/2004 | Green et al. |

FOREIGN PATENT DOCUMENTS

| JP | 2007-527857 | 10/2007 |
| JP | 2009-504784 | 2/2009 |
| WO | WO 2004/112839 | 12/2004 |
| WO | WO 2006/101845 | 9/2006 |
| WO | WO 2007/022494 | 2/2007 |

OTHER PUBLICATIONS

PCT International Search Report and Written Opinion for PCT/US2009/057363 completed Oct. 21, 2009.
Feng et al, *Med. Chem.*, Jan. 26, 2006, 49(2): 770-788.
Leamon et al., *Drug Discovery Today*, vol. 6, Issue 1, Jan. 1, 2001, 44-51.
Sun et al., *Journal of Biomedical Materials Research*, Part A, vol. 78A, Issue 3, Sep. 1, 2006, 550-557.
Vlahov et al., *Bioorganic & Medicinal Chemistry Letters*, vol. 16, Issue 19, Oct. 1, 2006, 5093-5096.
Westerhof, G. Robbin, *Molecular Pharmacology*, 1995, vol. 48, 459-471.

*Primary Examiner* — Jeffrey H Murray
(74) *Attorney, Agent, or Firm* — Finnegan, Henderson, Harabow, Garrett & Dunner, LLP

(57) ABSTRACT

Conjugates of antifolates, releasable linkers, and drugs, and pharmaceutical compositions containing them are described. The conjugates are useful for treating diseases arising from pathogenic cell populations. Methods for treating such diseases are also described.

1 Claim, 11 Drawing Sheets

FOLATE RECEPTOR BINDING CONJUGATES OF ANTIFOLATES

CROSS REFERENCE TO RELATED APPLICATIONS

This application is a continuation of U.S. Ser. No. 14/010,122, filed Aug. 26, 2013, pending, which is a continuation of U.S. Ser. No. 13/063,889, filed Mar. 14, 2011, now U.S. Pat. No. 8,546,425, which is a national stage entry under 35 U.S.C. §371 of International Application No. PCT/IB2009/57363, filed Sep. 17, 2009, which claims the benefit under 35 U.S.C. §119(e) of U.S. Provisional Application Ser. No. 61/097,655, filed Sep. 17, 2008, the entirety of the disclosure of each of which is incorporated herein by reference.

BACKGROUND AND SUMMARY OF THE INVENTION

Folic acid (FA), or vitamin B9, is an essential nutrient required by all living cells for proper metabolic maintenance of 1-carbon pathways as well as for nucleotide biosynthesis. This ligand displays extremely high affinity (KD~100 pM) for a cell surface-oriented glycoprotein called the folate receptor (FR), which is a glycosylphosphatidyinositol-linked protein that captures its ligands from the extracellular milieu. The folate receptor (FR) is a tumor-associated membrane protein that binds folic acid (FA) and is capable of transporting molecules bound to folic acid inside cells via an endocytosis mechanism. Immediately after binding, the plasma membrane surrounding the FR-ligand complex will invaginate to form an internal vesicle, called an endosome. The pH of the vesicle lumen is somewhat lowered through the action of proton pumps that are co-localized in the endosome membrane, and this acidification presumably mediates a conformational change in the FR protein to release its bound ligand to allow for cytosolic entry. The FR is also a recognized tumor antigen; and because of this, methods to exploit its presence and function have been explored for possible therapeutic value.

FR-α distribution in normal adult tissue is restricted to the apical membrane surface of some polarized epithelial cells, including lung, choroid plexus and some glandular tissue. Expression is also high in placental trophoblasts and on the luminal surface of proximal tubule kidney epithelial cells, the latter probably being important for the re-absorption of folates from the urine. However, Elevated expression of the FR-α occurs in several cancer types. Non-mucinous ovarian cancer (the majority of ovarian cancers) was the tumor type first to be associated with "over-expression". Several studies confirmed that ~80-90% of these tumors over-express FR-α. Other gynecological cancers (e.g. ~50% of serous uterine tumors) also over-express the receptor. Although the endometrioid histologic subtype may express the receptor less frequently, it is by far the most common form of uterine cancer. Therefore, it is believed herein that a considerable number of uterine cancer patients may benefit from some form of FR-targeted therapy. Other tumors reported to over-express FR-α to varying frequencies include pediatric ependymal brain tumors, breast, colon, renal and lung tumors, and mesothelioma.

Although it is generally accepted that FA can be conjugated to virtually any molecule to mediate delivery inside FR-positive cells, not all conjugates can be expected to bind to the FR with the same affinity. It is believed herein for example that large drugs that are linked in close proximity to the FA moiety may, perhaps due to steric interactions, alter the ability of FA to enter the binding pocket of the FR. Further, the nature of the drug may also be important, because intramolecular association with the FA might yield a poorly-binding conjugate that may not properly orient itself into the FR. In any case, after FA has delivered the molecule to the target site, it is no longer used. Therefore, it was recognized herein that targeting with a different molecule that had the potential to have a second function in treating a disease state would be useful.

It has been discovered herein that antifolates are also capable of targeting FR, and in conjunction with releasable linkers are also capable of targeted delivery of molecules to cells that express the FR. However, it has been reported that the relative affinity of such antifolates is widely varying, as determined at 4° C. which has hindered the use of antifolates as targeting ligands. It has also been unexpectedly discovered herein that the relative affinity of antifolates at the folate receptor, as compared to folic acid, is temperature dependent. Moreover, it has been discovered that the relative affinity of some antifolates increases with increasing temperature, while the relative affinity of other antifolates decreases with increasing temperature. Further, the relative affinity of still other antifolates is relatively invariant with increasing temperature.

Described herein are compounds, compositions, and methods that include conjugates comprising a folate receptor binding antifolate, at least one releasable linker, and one or more drugs, where the antifolate has a high relative affinity for the folate receptor, as compared to folic acid, at temperatures above 4° C., such as at temperatures above 20° C., at temperatures above 25° C., at temperatures above 30° C., and/or at temperatures that are physiologically relevant, such as physiological temperatures in mammals. Also described herein are compounds, compositions, and methods that include conjugates comprising a folate receptor binding antifolate, at least one releasable linker, and one or more drugs, where the conjugate has a high relative affinity for the folate receptor, as compared to folic acid, at temperatures above 4° C., such as at temperatures above 20° C., at temperatures above 25° C., at temperatures above 30° C. and/or at temperatures that are physiologically relevant, such as physiological temperatures in mammals. In general, the conjugates described herein are covalent conjugates; however, it is to be understood that the drugs forming part of the conjugates described herein may include other bond forms, including but not limited to complexes, such as metal chelates, and the like.

In one embodiment, compounds, compositions, and methods are described herein that include a conjugate comprising an antifolate having a relative affinity for the folate receptor, as compared to folic acid, of at least about 0.1, at least about 0.2, at least about 0.25, or at least about 0.5, at one or more of the temperatures described herein. In another embodiment, compounds, compositions, and methods are described herein that include a conjugate having a relative affinity for the folate receptor, as compared to folic acid, of at least about 0.05, at least about 0.1, at least about 0.2, at least about 0.25, or at least about 0.5, at one or more of the temperatures described herein.

In another embodiment, a method for evaluating the folate receptor binding ligand affinity for the FR is described herein. In one aspect, the binding affinity is relative and is compared with folic acid. It is to be understood that the assays described herein may be used to evaluate the relative selectivity and/or specificity of the binding to the folate receptor by competing the folate receptor binding ligand and/or conjugate with folic acid. It is appreciated that such relative affinities may be used to select molecules capable of binding to the FR and to select conjugates that include FR receptor binding moieties.

In another embodiment, compounds, compositions, and methods are described herein that include a drug delivery conjugate of the formula AL(D)$_m$ are described wherein A is a folate receptor binding antifolate; L is a monovalent or multivalent linker, comprising at least one releasable linker; each D is a drug; and m is an integer from 1 to about 3. It is to be understood that when m is greater than 1, each drug D is independently selected in each instance. In other words, D may be the same drug or be different drugs in each instance.

In another embodiment, the compositions and methods described herein are useful for treating one or more pathogenic populations of cells in a patient. The compositions include a therapeutically effective amount of one or more conjugates described herein, optionally in combination with one or more carriers, excipients, and/or diluents, or any combinations thereof. The methods include the step of administering an effective amount of one or more conjugates described herein and/or one or more compositions described herein. In another embodiment, the compositions and methods are useful for treating cancer, and other diseases.

In another embodiment, uses of the compounds and compositions in the manufacture of medicaments are described herein, where the medicaments include a therapeutically effective amount of one or more conjugates described herein and/or one or more compositions described herein for treating one or more pathogenic populations of cells in a patient. It is to be understood that the medicaments may be used in any of the methods described herein for treating one or more pathogenic populations of cells in a patient.

DETAILED DESCRIPTION

Figure 1:
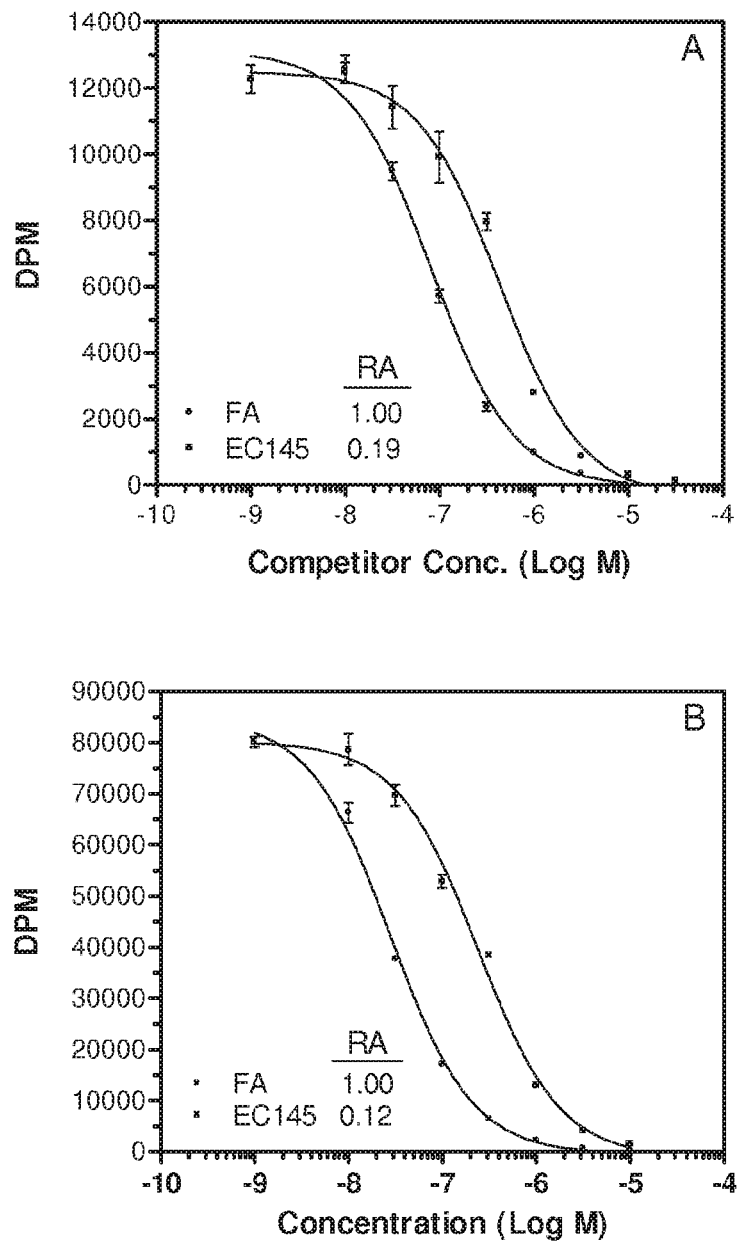
FIG. 1. Panel A, KB cell-based relative affinity assay. Panel B, cell-free relative affinity assay (isolated plate-bound folate receptor). Both assays were performed in the absence of serum while the plates were sitting on a bed of ice. FA, (●). EC145, (■).

In one embodiment, drug delivery conjugates of the formula

AL(D)$_m$ are described wherein A is a folate receptor binding antifolate; L is a monovalent or multivalent linker, comprising at least one releasable linker; each D is a drug; and m is an integer from 1 to about 3. It is to be understood that when m is greater than 1, each D may be the same drug or be a different drug from another in each instance. In another embodiment, the monovalent or multivalent linker L includes at least two releasable linkers. In one variation of each of the foregoing, the monovalent or multivalent linker includes at least one releasable linker that is not a disulfide.

In another embodiment, the conjugates described herein include an antifolate having a relative affinity for the folate receptor, as compared to folic acid, of at least about 0.1, at least about 0.2, at least about 0.25, or at least about 0.5, at one or more of the temperatures described herein. In another embodiment, the conjugates described herein have a relative affinity for the folate receptor, as compared to folic acid, of at least about 0.05, at least about 0.1, at least about 0.2, at least about 0.25, or at least about 0.5, at one or more of the temperatures described herein. In another embodiment, the compounds, compositions, and methods that include conjugates comprising a folate receptor binding antifolate, at least one releasable linker, and one or more drugs, where the antifolate has a high relative affinity for the folate receptor, as compared to folic acid, at temperatures above 4° C., such as at temperatures above 20° C., at temperatures above 25° C. at temperatures above 30° C., and/or at temperatures that are physiologically relevant, such as physiological temperatures in mammals. Also described herein are compounds, compositions, and methods that include conjugates comprising a folate receptor binding antifolate, at least one releasable linker, and one or more drugs, where the conjugate has a high relative affinity for the folate receptor, as compared to folic acid, at temperatures above 4° C., such as at temperatures above 20° C., at temperatures above 25° C., at temperatures above 30° C., and/or at temperatures that are physiologically relevant, such as physiological temperatures in mammals. In general, the conjugates described herein are covalent conjugates; however, it is to be understood that the drugs forming part of the conjugates described herein may include other bond forms, including but not limited to complexes, such as metal chelates, and the like.

It is to be understood that the determination of the relative affinity of the antifolates and/or conjugates described herein may be performed by any conventional method, or alternatively by the methods described herein adapted for measuring relative affinity at temperatures above 4° C., such as at temperatures above 20° C. at temperatures above 25° C. at temperatures above 30° C. and/or at temperatures that are physiologically relevant, such as physiological temperatures in mammals.

As used herein, the term "antifolate" generally refers to any compound that is an inhibitor, antagonist or other modulator of folate metabolism, such as inhibition and/or antagonism of dihydrofolate reductase (DHFR), glycinamide ribonucleotide transformylase (GARTF), folylpolyglutamate synthetase (FPGS), and thymidylate synthase (TS), or a folate receptor antagonist. It is appreciated that antifolates may bind to the folate binding site in any of the above, or to another site that influences binding of folate or another compound to the folate binding site of any of the above. As used herein, the term "folate receptor binding" generally refers to compounds that selectively or specifically bind to the folate receptor.

In another embodiment the folate receptor binding antifolate is selected from LV, L-leucovorin (L-5-formyltetrahydrofolate); 5-CH3-THF, 5-methyltetrahydrofolate; FA, folic acid; PteGlu, pteroyl glutamate (FA): MTX, methotrexate: 2-dMTX, 2-desamino-MTX; 2-CH3-MTX, 2-desamino-2-methyl-MTX: AMT, aminopterin; 2-dAMT, 2-desamino-AMT: 2-CH3-AMT, 2-desamino-2-methyl-AMT; 10-EdAM, 10-ethyl-10-deazaaminopterin; PT523. Nα-(4-amino-4-deoxypteroyl)-Nδ-(hemiphthaloyl)-L-ornithine: DDATHF, 5,10-dideaza-5,6,7,8,-tetrahydrofolic acid; 5-d(i)H4PteGlu, 5-deaza-5,6,7,8-tetrahydroisofolic acid; N9-CH3-5-d(i)H4PteGlu, N9-methyl-5-deaza-5,6,7,8-tetrahydroisofolic acid; 5-dPteHCysA, Nα-(5-deazapteroyl)-L-homocysteic acid; 5-dPteAPBA, Nα-(5-deazapteroyl)-DL-2-amino-4-phosphonobutanoic acid; 5-dPteOrn, Nα-(5-deazapteroyl)-L-ornithine; 5-dH4PteHCysA, Nα-(5-deaza-5,6,7,8-tetrahydropteroyl)-L-homocysteic acid: 5-dH4PteAPBA, Nα-(5-deaza-5,6,7,8-tetrahydropteroyl)-DL-2-amino-4-phosphobutanoic acid; 5-dH4PteOrn, Nα-(5-deaza-5,6,7,8-tetrahydropteroyl)-L-ornithine; CB3717, N10-propargyl-5,8-dideazafolic acid; ICI-198,583, 2-desamino-2-methyl-N10-propargyl-5,8-dideazafolic acid; 4-H-ICI-198,583, 4-deoxy-ICI-198,583; 4-OCH3-ICI-198,583, 4-methoxy-ICI-198,583; Glu-to-Val-ICI-198,583; valine-ICI-198; 583; Glu-to-Sub-ICI-198,583, 2-amino-suberate-ICI-198,583; 7-CH3-ICI-198,583, 7-methyl-ICI-198,583; ZD1694, N-[5(N-(3,4-dihydro-2-methyl-4-oxoquinazolin-6-yl-methyl)amino)2-thienyl)]-L-glutamic acid; 2-NH2-ZD1694, 2-amino-ZD1694; BW1843 U89, (S)-2[5-(((1,2-dihydro-3-methyl-1-oxobenzo(f)quinazolin-9-yl)methyl) amino)-1-oxo-2-isoindolinyl]-glutaric acid; LY231514, N-(4-(2-(2-amino-4,7-dihydro-4-oxo-3H-pyrrolo[2,3-D]pyrimidin-5-yl)ethyl)benzoyl]-L-glutamic acid: IAHQ, 5,8-dideazaisofolic acid; 2-dIAHQ, 2-desamino-IAHQ; 2-CH3-dIAHQ, 2-desamino-2-methyl-IAHQ; 5-d(i)PteGlu, 5-deazaaisofolic acid: N9-CH3-5-d(i)PteGlu, N9-methyl-5-deazaisofolic acid; N9-CHO-5-d(i)PteGlu, N9-formyl-5-deazaisofolic acid: AG337, 3,4-dihydro-2-amino-6-methyl-4-oxo-5-(4-pyridylthio)quinazoline; and AG377, 2,4-diamino-6-[N-(4-(phenylsulfonyl)benzyl)ethyl)amino]quinoline.

In another embodiment the folate receptor binding antifolate is selected from aminopterin, methotrexate, raltitrexed (also referred to as TOMUDEX, ZD1694), plevitrexed (also referred to as BGC 9331; ZD9331), pemetrexed (also referred to as ALIMTA, LY231514), lometrexol (5,10-dideazatetrahydrofolic acid) and related cyclopenta[g]quinazolines with dipeptide ligands, CB3717, CB300945 (also referred to as BGC 945) and stereoisomers thereof such as 6-R,S-BGC 945, CB300638 (also referred to as BGC 638), and BW1843U89. The preparation of illustrative antifolates are described in Bavetsias et al., 2000: Bavetsias et al., 2002: Gibbs et al., 2005: Henderson et al., 2006; Jackman et al., 2004; and Theti et al., 2003. The foregoing publications, and each additional publication cited herein is incorporated herein by reference. In another embodiment, the folate receptor binding antifolate is selected from aminopterin, methotrexate, CB3717, plevitrexed, raltitrexed. BGC 945, pemetrexed, and the like. In another embodiment, the antifolate is selected from CB3717, plevitrexed, raltitrexed, and 5-Me-THF. In another embodiment, the antifolate is selected from BGC 945, BGC 638, and BGC 9331.

In another embodiment, the antifolate is a compound having a relative affinity for the folate receptor of about 0.1 or greater at a temperature of about 20° C. or greater. In another embodiment, the antifolate is selected from 2-CH3-dIAHQ, 5-dPteAPBA, 5-dPteOrn, N9-CHO-5-d(i)PteGlu, 2-dIAHQ, 7-CH3-ICI-198583, Glu-to-Val-ICI-198583, Glu-to-Sub-ICI-198583, 4-MeO-ICI-198583, ICI-198583, 5-dH4PteHCysA. N9-CH3-5-d(i)H4PteGlu, 5-d(i)H4PteGlu, 5-CH3-THF, N9-CH3-5-d(i)PteGlu, 5-d(i)PteGlu, IAHQ, LY231514, BW1843U89, 2-NH2-ZD1694, ZD1694, CB3717, 5-dH4PteOrn, 5-dH4PteAPBA, 5-dPteHCysA, and DDATHF.

In another embodiment, the antifolate is a compound having a relative affinity for the folate receptor of about 0.2 or greater at a temperature of about 20° C. or greater. In another embodiment, the antifolate is selected from N9-CHO-5-d(i)PteGlu, 2-dIAHQ, 7-CH3-ICI-198583, Glu-to-Val-ICI-198583. Glu-to-Sub-ICI-198583, 4-MeO-ICI-198583, ICI-198583, 5-dH4PteHCysA, N9-CH3-5-d(i)H4PteGlu, 5-d(i)H4PteGlu, 5-CH3-THF, N9-CH3-5-d(i)PteGlu, 5-d(i)PteGlu, IAHQ, LY231514, BW1843U89, 2-NH2-ZD1694, ZD1694, CB3717, 5-dH4PteOrn, 5-dH4PteAPBA, 5-dPteHCysA, and DDATHF.

In another embodiment, the antifolate is a compound having a relative affinity for the folate receptor of about 0.5 or greater at a temperature of about 20° C. or greater. In another embodiment, the antifolate is selected from N9-CH3-5-d(i)PteGlu, 5-d(i)PteGlu, IAHQ, LY231514, BW1843U89, 2-NH2-ZD1694, ZD1694, CB3717, 5-dH4PteOrn, 5-dH4PteAPBA, 5-dPteHCysA, and DDATHF.

In another embodiment, the antifolate is selected from 5-dPteAPBA, 5-dPteOrn, and 2-CH3-IAHQ. In another embodiment, the antifolate is selected from 5-d(i)H4PteGlu, N9-CH3-5-d(i)H4PteGlu, ICI-198583, 4-MeO-ICI-198583, Glu-to-Val-ICI-198583, Glu-to-Sub-ICI-198583, 7-CH3-ICI-198583, N9-CHO-5-d(i)PteGlu, and 2d-IAHQ. In another embodiment, the antifolate is selected from 5-d(i)PteGlu, N9-CH3-5-d(i)PteGlu, pemetrexed, CB3717, ralitrexed, 2-desmethyl-2-NH2-ralitrexed, BW1834U89, IAHQ, 5-dH4PteHCysA, dH4PteAPBA, dH4PteOrn, and DDATHF.

In another embodiment, the antifolate is a deaza or dideaza analog of folate, including reduced derivatives thereof. In another embodiment, the antifolate is CB3717. In another embodiment, the antifolate is 5-Me-THF.

Alternatively, in another embodiment, the antifolate is not leucovorin. Alternatively, in another embodiment, the antifolate is not pteroic acid. Alternatively, in another embodiment, the antifolate is not pemetrexed. Alternatively, in another embodiment, the antifolate is not methotrexate.

In another embodiment, the antifolate is a compound of the formula:

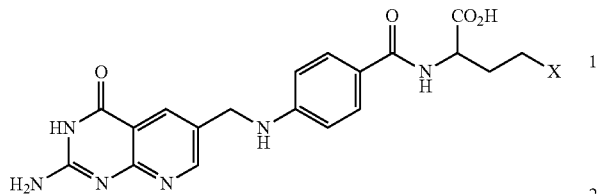

wherein X=PO(OH)$_2$ (5-dPteAPBA). CH$_2$NH$_2$ (5-dPteOrn), or SO$_2$OH (5-dPteHCysA).

In another embodiment, the antifolate is a compound of the formula:

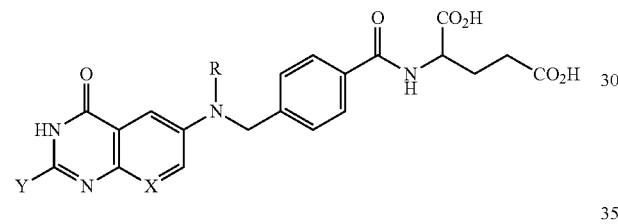

wherein X=N, Y=NH$_2$, R=H (5-d(i)PteGlu), X=N, Y=NH$_2$, R=CH$_3$ (N$^9$—CH$_3$-5-d(i)PteGlu), X=N, Y=NH$_2$, R=CHO(N$^9$—CHO-5-d(i)PteGlu). X=CH, Y=NH$_2$, R=H (IAHQ), X=CH, Y=H, R=H (2-dIAHQ), or X=CH, Y=CH3, R=H (2-CH$_3$-dIAHQ).

In another embodiment, the antifolate is a compound of the formula:

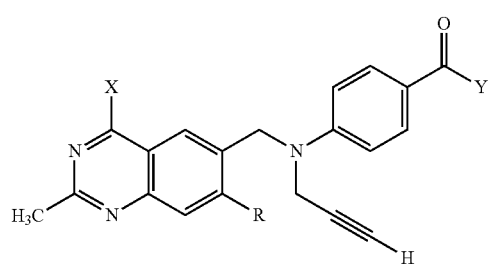

wherein X=OH, R=H, Y=Glu (ICI-198583), X=OCH$_3$, R=H, Y=Glu (4-MeO-ICI-198583), X=OH, R=H, Y=Valine (Glu-to-Val-ICI-198583), X=OH, R=H, Y=Suberate (Glu-Sub-ICI-198583), or X=OH, R=CH3, Y=Glu (7-CH$_3$—ICI-198583).

In another embodiment, the antifolate is a compound of the formula:

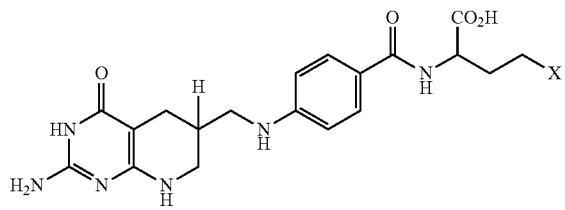

wherein X=PO(OH)$_2$ (5-dH$_4$PteAPBA), CH$_2$NH$_2$ (5-dH$_4$PteOm), or SO$_2$OH (5-dH$_4$PteHCysA).

In another embodiment, the antifolate is a compound of the formula:

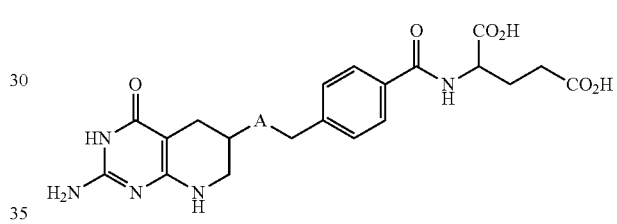

wherein A=NH (5-d(i)H$_4$PteGlu), NCH$_3$ (N$^9$—CH3-5-d(i)H$_4$PteGlu), or CH$_2$ (DDATHF).

In another embodiment, the antifolate is a BW1834U89, of the following formula:

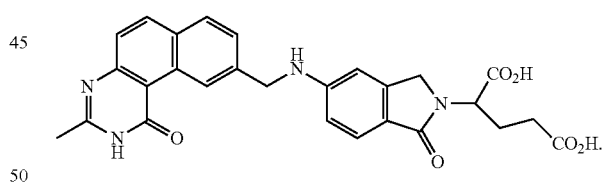

In another embodiment, the antifolate is BGC 945 (R=CH$_2$OH) or BGC 638 (R=CH$_3$) of the following formula.

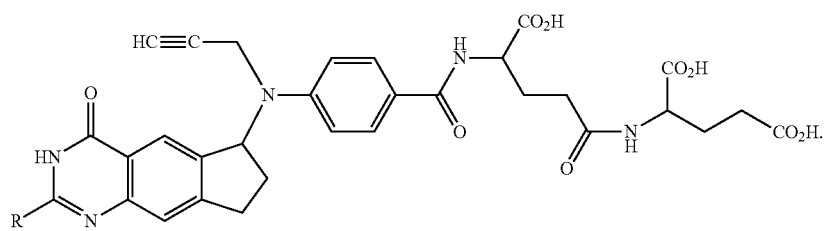

In one variation, the absolute stereochemistry of these antifolates is L-Glu-D-Glu.

In another embodiment, the antifolate is a compound of the formula:

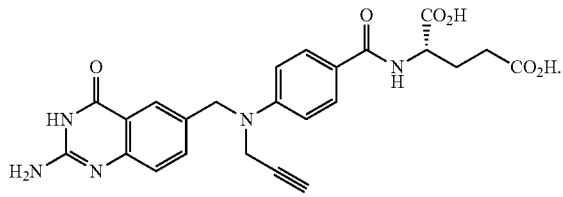 [SMILES: C#CCN(Cc1ccc2nc(N)[nH]c(=O)c2c1)c1ccc(C(=O)N[C@@H](CCC(=O)O)C(=O)O)cc1]

Additional antifolates are described in Gangjee et al., J Med Chem 10.1021/jm800244v (2008), the disclosure of which is incorporated herein by reference.

In another embodiment, in each of the foregoing compounds that includes a glutamate radical, the corresponding analogs are also described herein where one or more amino acids, as described herein, replaces the glutamate. It is to be understood that such amino acids replacing glutamate may be naturally occurring, such as Asp, Cys, Ser, Thr, Lys, and the like, or may be unnatural, including but not limited to unnatural absolute configurations, beta amino acids, unnatural side chains, and the like. In another embodiment, at least one of the amino acids replacing glutamate is charged. In another embodiment, Glu is replaced by the dipeptide (L-Glu-γ-D-Glu) moiety.

The drug can be any molecule capable of modulating or otherwise modifying cell function, including pharmaceutically active compounds. Suitable molecules can include, but are not limited to: peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents: cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers: anti-depressants; H-2 antagonists: anticonvulsants; antinauseants; prostaglandins and prostaglandin analogs; muscle relaxants: stimulants; decongestants; antiemetics; diuretics; antispasmodics; antiasthmatics; anti-Parkinson agents; expectorants; cough suppressants; and mucolytics.

Further, the drug can be any drug known in the art which is cytotoxic, enhances tumor permeability, inhibits tumor cell proliferation, promotes apoptosis, decreases anti-apoptotic activity in target cells, is used to treat diseases caused by infectious agents, or is useful for treating a disease state caused by any type of pathogenic cell. Drugs suitable for use in accordance with this invention include alkylating agents, antiandrogens, antiestrogens, androgens, aclamycin and aclamycin derivatives, estrogens, antimetabolites such as cytosine arabinoside, purine analogs, pyrimidine analogs, busulfan, carboplatin, chlorambucil, cisplatin and other platinum compounds, tamoxiphen, taxol, paclitaxel, paclitaxel derivatives, Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, analogs and derivative thereof such as deacetylvinblastine monohydrazide, and other vinca alkaloids, including those described in PCT international publication No. WO 2007/022493, the disclosure of which is incorporated herein by reference, colchicine, colchicine derivatives, allocolchicine, thiocolchicine, trityl cysteine, Halicondrin B, dolastatins such as dolastatin 10, amanitins such as α-amanitin, camptothecin, irinotecan, and other camptothecin derivatives thereof, maytansines, geldanamycin and geldanamycin derivatives, estramustine, nocodazole, MAP4, colcemid, peptide and peptidomimetic signal transduction inhibitors, and any other drug or toxin. Other drugs that can be used in accordance with the invention include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, and any other antimicrobial compound.

In another embodiment, the drug is a vinca alkaloid, including but not limited to vinblastine, vincristine, vindesine, and the like, and analogs and derivatives thereof. In another embodiment, the drug is a tubulysin, and analogs and derivatives thereof. In another embodiment, the drug is a epothilone, and analogs and derivatives thereof. In another embodiment, the drug is a mitomycin, and analogs and derivatives thereof. In one selection of each of the foregoing embodiments, the antifolate is EC282.

In another embodiment, processes for preparing the compounds are described herein. Illustratively, EC0284 is prepared as follows:

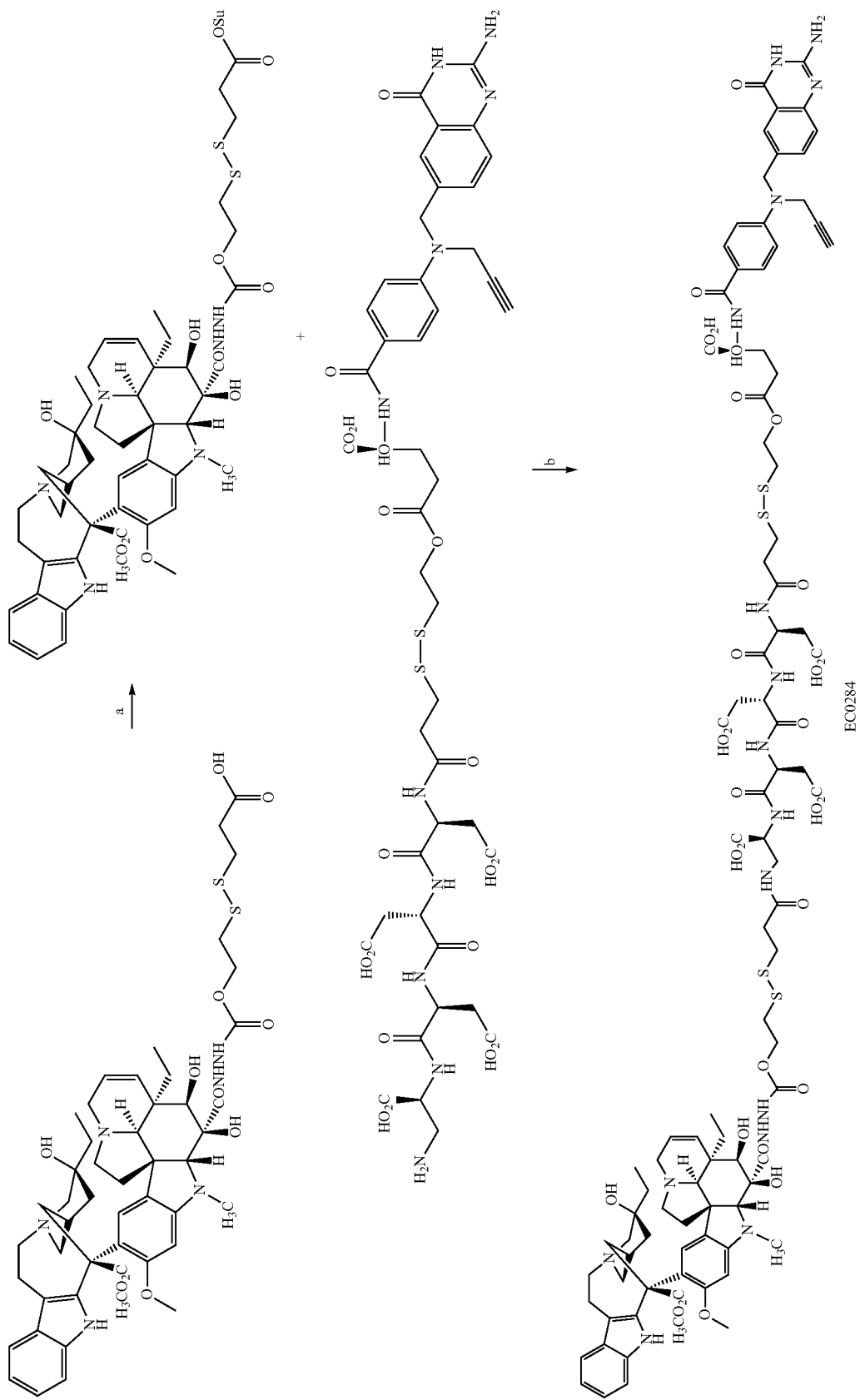

Although illustrated for EC0284, it is to be understood that the foregoing illustrative synthesis may be routinely modified and adapted to prepare other compounds described herein by the appropriate selection of starting materials.

The monovalent or multivalent linker is any chain of atoms having two or more points of attachment for connecting the antifolate that the one or more drugs, and which may be linear, branched, or cyclic, or alternatively include one or more cyclic regions. Illustratively, the linker comprises C, N, O, P, S, and Si. The monovalent or multivalent linker also includes at least one releasable linker.

The term "releasable linker" as used herein generally refers to a linker that includes at least one bond that can be broken under physiological conditions (e.g., a pH-labile, acid-labile, oxidatively-labile, and/or enzyme-labile bond). It should be appreciated that such physiological conditions resulting in bond breaking include standard chemical hydrolysis reactions that occur, for example, at physiological pH, or as a result of compartmentalization into a cellular organelle such as an endosome having a lower pH than cytosolic pH. In one variation, the physiological conditions are those found in an endosome.

The cleavable bond or bonds may be present in the interior of a cleavable linker and/or at one or both ends of a cleavable linker. In other words, the releasable linker may contain the scissile bond or may be connected to another linker, such as a spacer linker, or alternatively to a drug or the antifolate via the scissile bond. It is appreciated that the lability of the cleavable bond may be adjusted by including functional groups or fragments within the linker L that are able to assist or facilitate such bond breakage, also termed anchimeric assistance. In addition, it is appreciated that additional functional groups or fragments may be included within the polyvalent linker L that are able to assist or facilitate additional fragmentation of the receptor binding ligand agent conjugates after bond breaking of the releasable linker. The lability of the cleavable bond can be adjusted by, for example, substitutional changes at or near the cleavable bond, such as including alpha branching adjacent to a cleavable disulfide bond, increasing the hydrophobicity of substituents on silicon in a moiety having a silicon-oxygen bond that may be hydrolyzed, homologating alkoxy groups that form part of a ketal or acetal that may be hydrolyzed, and the like. It is also to be understood that such linkers contain more than one releasable linker. For example, self-immolative linkers are described herein that contain more than one releasable linker.

Accordingly, it is to be understood that a cleavable bond can connect two adjacent atoms within the releasable linker and/or connect other linkers or A and/or D, as described herein, at either or both ends of the releasable linker. In the case where a cleavable bond connects two adjacent atoms within the releasable linker, following breakage of the bond, the releasable linker is broken into two or more fragments. Alternatively, in the case where a cleavable bond is between the releasable linker and another moiety, such as an additional heteroatom, additional spacer linker, another releasable linker, the antifolate A, or a drug D, following breakage of the bond, the releasable linker is separated from the other moiety.

In another embodiment, the linker L includes a disulfide releasable linker. In another embodiment, the linker L includes at least one releasable linker that is not a disulfide releasable linker. In another embodiment, the linker L includes at least two releasable linkers. In another embodiment, the linker L includes at least two releasable linkers, where at least one releasable linker is not a disulfide releasable linker. In another embodiment, the linker L includes at least two releasable linkers, where at least one releasable linker is separates each drug D from the antifolate.

In another embodiment, the releasable and spacer linkers may be arranged in such a way that subsequent to the cleavage of a bond in the bivalent linker, released functional groups chemically assist the breakage or cleavage of additional bonds, also termed anchimeric assisted cleavage or breakage. It is to be understood that such releasable linkers contain at least two releasable linkers. An illustrative embodiment of such a bivalent linker or portion thereof includes compounds having the formulae:

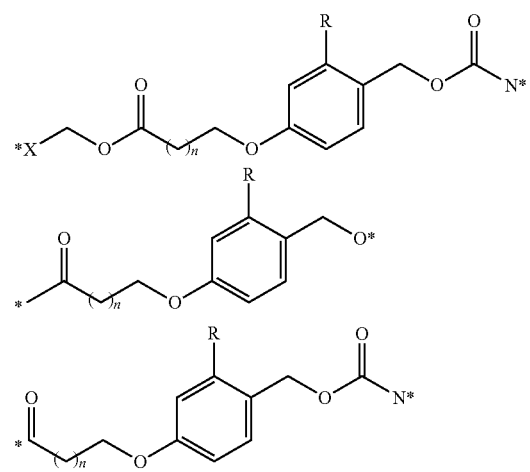

where X is an heteroatom, such as nitrogen, oxygen, or sulfur, or a carbonyl group; n is an integer selected from 0 to 4; illustratively 2; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the bivalent linker, or alternatively for attachment of the drug, or analog or derivative thereof, or the antifolate, or analog or derivative thereof. In one embodiment, n is 2 and R is methoxy. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

Illustrative mechanisms for cleavage of the bivalent linkers described herein include the following 1,4 and 1,6 fragmentation mechanisms

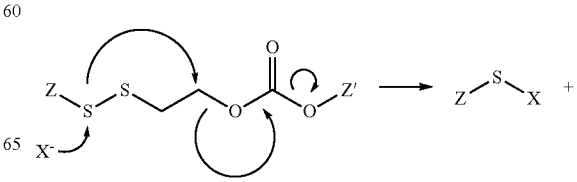

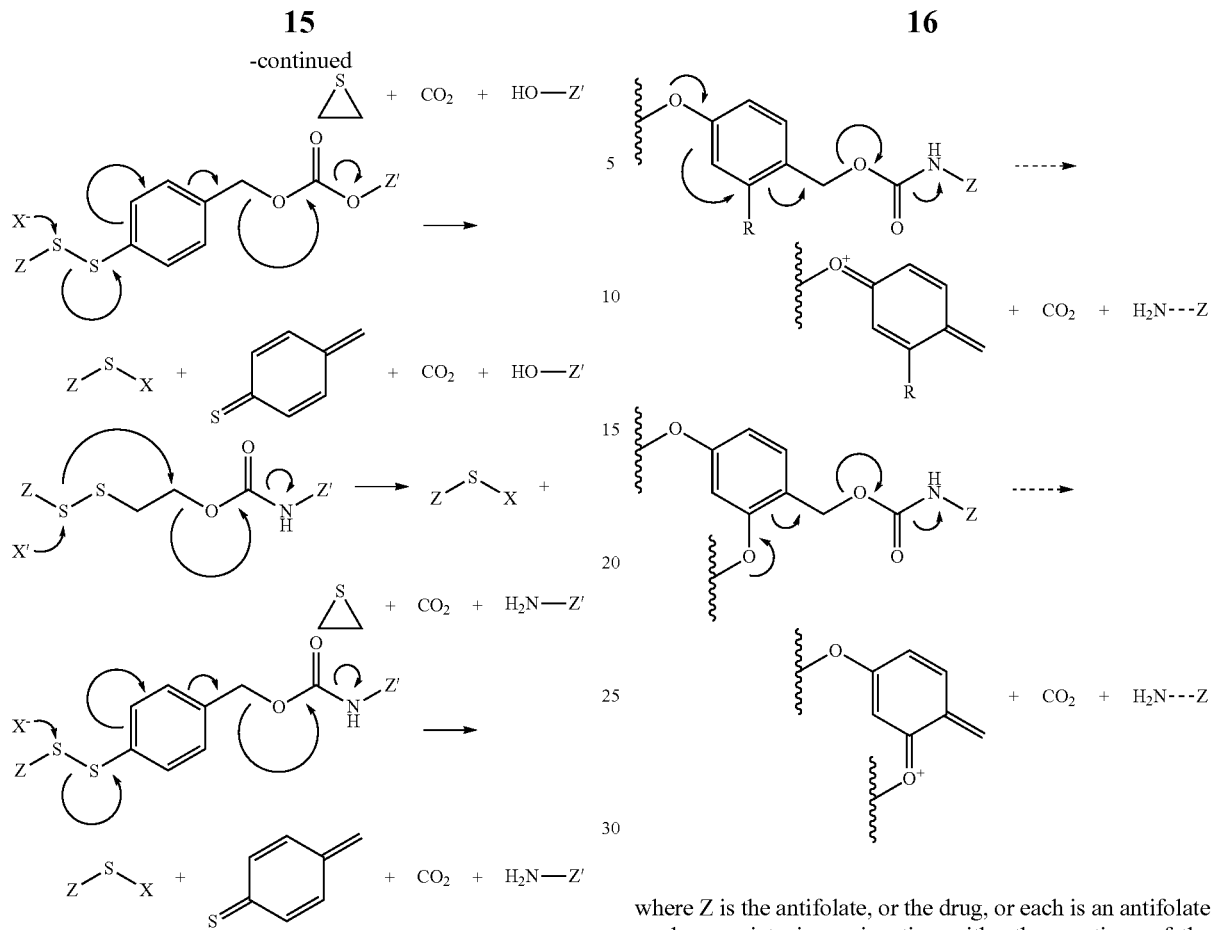

where X is an exogenous or endogenous nucleophile, glutathione, or bioreducing agent, and the like, and either of Z or Z' is the antifolate, or the drug, or am antifolate or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present.

Other illustrative mechanisms for bond cleavage of the releasable linker include oxonium-assisted cleavage as follows:

where Z is the antifolate, or the drug, or each is an antifolate or drug moiety in conjunction with other portions of the polyvalent linker, such as a drug or antifolate moiety including one or more spacer linkers and/or other releasable linkers. Without being bound by theory, in this embodiment, acid catalysis, such as in an endosome, may initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base.

Other illustrative linkers include compounds of the formulae:

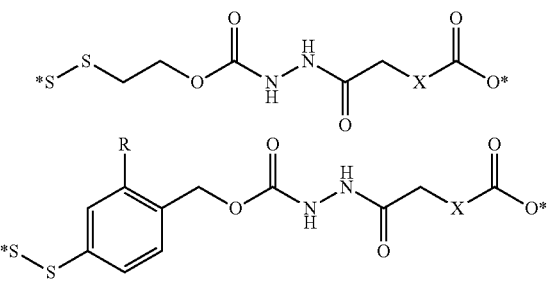

where X is NH, $CH_2$, or O; R is hydrogen, or a substituent, including a substituent capable of stabilizing a positive charge inductively or by resonance on the aryl ring, such as alkoxy and the like, including methoxy; and the symbol (*) indicates points of attachment for additional spacer, heteroatom, or releasable linkers forming the bivalent linker, or alternatively for attachment of the drug, or the antifolate.

Illustrative mechanisms for cleavage of such bivalent linkers described herein include the following 1,4 and 1,6 fragmentation mechanisms followed by anchimerically assisted cleavage of the acylated Z' via cyclization by the hydrazide group:

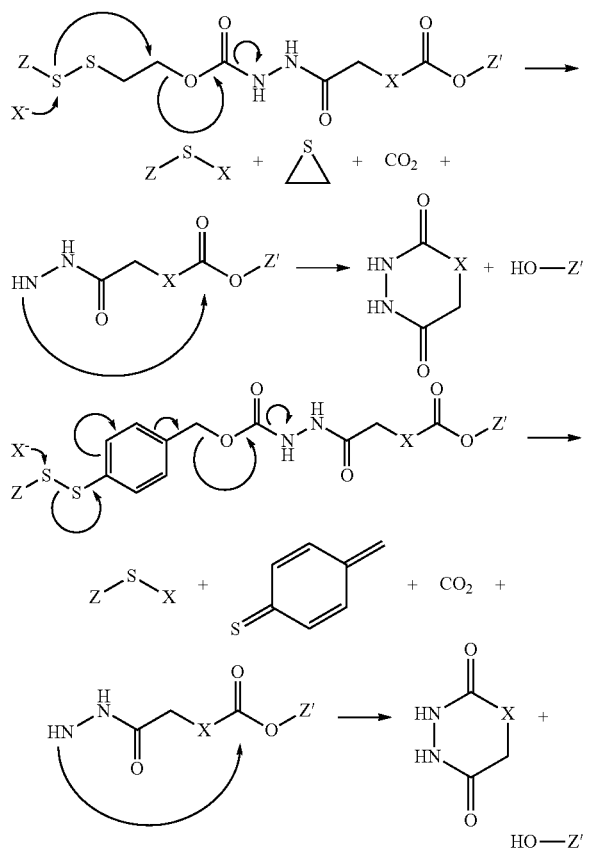

where X is an exogenous or endogenous nucleophile, glutathione, or bioreducing agent, and the like, and either of Z or Z' is the antifolate, or the drug, or an antifolate or drug moiety in conjunction with other portions of the polyvalent linker. It is to be understood that although the above fragmentation mechanisms are depicted as concerted mechanisms, any number of discrete steps may take place to effect the ultimate fragmentation of the polyvalent linker to the final products shown. For example, it is appreciated that the bond cleavage may also occur by acid-catalyzed elimination of the carbamate moiety, which may be anchimerically assisted by the stabilization provided by either the aryl group of the beta sulfur or disulfide illustrated in the above examples. In those variations of this embodiment, the releasable linker is the carbamate moiety. Alternatively, the fragmentation may be initiated by a nucleophilic attack on the disulfide group, causing cleavage to form a thiolate. The thiolate may intermolecularly displace a carbonic acid or carbamic acid moiety and form the corresponding thiacyclopropane. In the case of the benzyl-containing polyvalent linkers, following an illustrative breaking of the disulfide bond, the resulting phenyl thiolate may further fragment to release a carbonic acid or carbamic acid moiety by forming a resonance stabilized intermediate. In any of these cases, the releasable nature of the illustrative polyvalent linkers described herein may be realized by whatever mechanism may be relevant to the chemical, metabolic, physiological, or biological conditions present. Without being bound by theory, in this embodiment, acid catalysis, such as in an endosome, may also initiate the cleavage via protonation of the urethane group. In addition, acid-catalyzed elimination of the carbamate leads to the release of $CO_2$ and the nitrogen-containing moiety attached to Z, and the formation of a benzyl cation, which may be trapped by water, or any other Lewis base, as is similarly described herein.

In another embodiment, the polyvalent linkers described herein are compounds of the following formulae

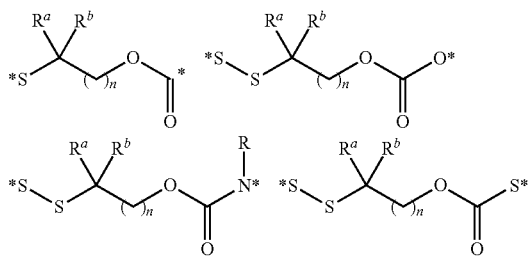

where n is an integer selected from 1 to about 4; $R^a$ and $R^b$ are each independently selected from the group consisting of hydrogen and alkyl, including lower alkyl such as $C_1$-$C_4$ alkyl that are optionally branched; or $R^a$ and $R^b$ are taken together with the attached carbon atom to form a carbocyclic ring: R is an optionally substituted alkyl group, an optionally substituted acyl group, or a suitably selected nitrogen protecting group: and (*) indicates points of attachment for the drug, or antifolate, other polyvalent linkers, or other parts of the conjugate.

In another embodiment, the polyvalent linkers described herein include compounds of the following formulae

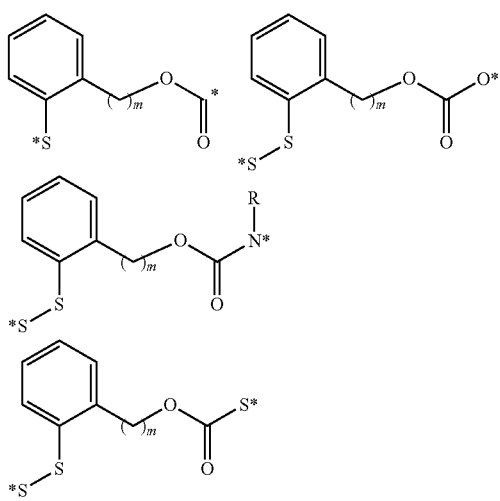

where m is an integer selected from 1 to about 4; R is an optionally substituted alkyl group, an optionally substituted acyl group, or a suitably selected nitrogen protecting group; and (*) indicates points of attachment for the drug, antifolate, other polyvalent linkers, or other parts of the conjugate.

In another embodiment, the polyvalent linkers described herein include compounds of the following formulae

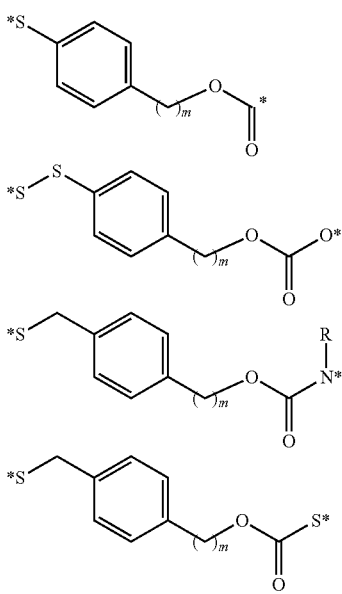

where m is an integer selected from 1 to about 4; R is an optionally substituted alkyl group, an optionally substituted acyl group, or a suitably selected nitrogen protecting group; and (*) indicates points of attachment for the drug, antifolate, other polyvalent linkers, or other parts of the conjugate.

Another illustrative mechanism involves an arrangement of the releasable and spacer linkers in such a way that subsequent to the cleavage of a bond in the bivalent linker, released functional groups chemically assist the breakage or cleavage of additional bonds, also termed anchimeric assisted cleavage or breakage. An illustrative embodiment of such a bivalent linker or portion thereof includes compounds having the formula:

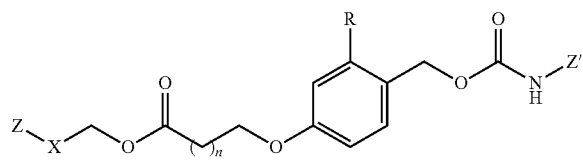

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and either of Z or Z' is the antifolate, or the drug, or an antifolate or drug moiety in conjunction with other portions of the bivalent linker. It is appreciated that other substituents may be present on the aryl ring, the benzyl carbon, the carbamate nitrogen, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

In this embodiment, the hydroxyalkanoic acid, which may cyclize, facilitates cleavage of the methylene bridge, by for example an oxonium ion, and facilitates bond cleavage or subsequent fragmentation after bond cleavage of the releasable linker. Alternatively, acid catalyzed oxonium ion-assisted cleavage of the methylene bridge may begin a cascade of fragmentation of this illustrative bivalent linker, or fragment thereof. Alternatively, acid-catalyzed hydrolysis of the carbamate may facilitate the beta elimination of the hydroxyalkanoic acid, which may cyclize, and facilitate cleavage of methylene bridge, by for example an oxonium ion. It is appreciated that other chemical mechanisms of bond breakage or cleavage under the metabolic, physiological, or cellular conditions described herein may initiate such a cascade of fragmentation. It is appreciated that other chemical mechanisms of bond breakage or cleavage under the metabolic, physiological, or cellular conditions described herein may initiate such a cascade of fragmentation.

In another embodiment, the releasable and spacer linkers may be arranged in such a way that subsequent to the cleavage of a bond in the polyvalent linker, released functional groups chemically assist the breakage or cleavage of additional bonds, also termed anchimeric assisted cleavage or breakage. An illustrative embodiment of such a polyvalent linker or portion thereof includes compounds having the formula:

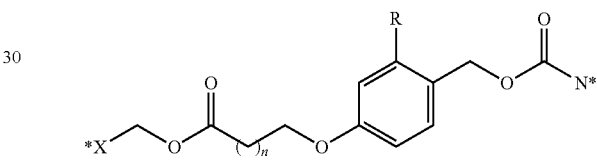

where X is an heteroatom, such as nitrogen, oxygen, or sulfur, n is an integer selected from 0, 1, 2, and 3, R is hydrogen, or a substituent, including a substituent capable of stabilizing a positive charge inductively or by resonance on the aryl ring, such as alkoxy, and the like, and the symbol (*) indicates points of attachment for additional spacer, heteroatom, or releasable linkers forming the polyvalent linker, or alternatively for attachment of the drug, or the antifolate. It is appreciated that other substituents may be present on the aryl ring, the benzyl carbon, the alkanoic acid, or the methylene bridge, including but not limited to hydroxy, alkyl, alkoxy, alkylthio, halo, and the like. Assisted cleavage may include mechanisms involving benzylium intermediates, benzyne intermediates, lactone cyclization, oxonium intermediates, beta-elimination, and the like. It is further appreciated that, in addition to fragmentation subsequent to cleavage of the releasable linker, the initial cleavage of the releasable linker may be facilitated by an anchimerically assisted mechanism.

Another illustrative embodiment of the linkers described herein, include releasable linkers that cleave under the conditions described herein by a chemical mechanism involving beta elimination. In one aspect, such releasable linkers include beta-thio, beta-hydroxy, and beta-amino substituted carboxylic acids and derivatives thereof, such as esters, amides, carbonates, carbamates, and ureas. In another aspect, such releasable linkers include 2- and 4-thioarylesters, carbamates, and carbonates.

In another illustrative embodiment, the linker includes one or more amino acids. In one variation, the linker includes a single amino acid. In another variation, the linker includes a peptide having from 2 to about 50, 2 to about 30, or 2 to about 20 amino acids. In another variation, the linker includes a peptide having from about 4 to about 8 amino acids. Such amino acids are illustratively selected from the naturally occurring amino acids, or stereoisomers thereof. The amino acid may also be any other amino acid, such as any amino acid having the general formula:

where R is hydrogen, alkyl, acyl, or a suitable nitrogen protecting group. R' and R" are hydrogen or a substituent, each of which is independently selected in each occurrence, and q is an integer such as 1, 2, 3, 4, or 5. Illustratively. R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. In another embodiment, R' and/or R" independently correspond to, but are not limited to, hydrogen or analogs of the side chains present on naturally occurring amino acids, such as the corresponding amino analogs of serine and threonine, such as beta-aminoalanine. The above described formula includes all stereoisomeric variations. For example, the amino acid may be selected from asparagine, aspartic acid, cysteine, glutamic acid, lysine, glutamine, arginine, serine, ornithine, threonine, and the like. In one variation, the releasable linker includes at least 2 amino acids selected from asparagine, aspartic acid, cysteine, glutamic acid, lysine, glutamine, arginine, serine, ornithine, and threonine. In another variation, the releasable linker includes between 2 and about 5 amino acids selected from asparagine, aspartic acid, cysteine, glutamic acid, lysine, glutamine, arginine, serine, ornithine, and threonine. In another variation, the releasable linker includes a tripeptide, tetrapeptide, pentapeptide, or hexapeptide consisting of amino acids selected from aspartic acid, cysteine, glutamic acid, lysine, arginine, and ornithine, and combinations thereof.

The term amino acid as used herein refers generally to aminoalkylcarboxylate, where the alkyl radical is optionally substituted, such as with alkyl, hydroxy alkyl, sulfhydrylalkyl, aminoalkyl, carboxyalkyl, and the like, including groups corresponding to the naturally occurring amino acids, such as serine, cysteine, methionine, aspartic acid, glutamic acid, and the like. It is to be understood that such amino acids may be of a single stereochemistry or a particular mixture of stereochemistries, including racemic mixtures. In addition, amino acid refers to beta, such as beta alanine, and the like, gamma, and longer amino acids, such as amino acids of the formula:

where R is hydrogen, alkyl, acyl, or a suitable nitrogen protecting group, R' and R" are hydrogen or a substituent, each of which is independently selected in each occurrence, and q is an integer such as 1, 2, 3, 4, or 5. Illustratively. R' and/or R" independently correspond to, but are not limited to, hydrogen or the side chains present on naturally occurring amino acids, such as methyl, benzyl, hydroxymethyl, thiomethyl, carboxyl, carboxylmethyl, guanidinopropyl, and the like, and derivatives and protected derivatives thereof. The above described formula includes all stereoisomeric variations. For example, the amino acid may be selected from asparagine, aspartic acid, cysteine, glutamic acid, lysine, glutamine, arginine, serine, ornithine, threonine, and the like. In another illustrative aspect of the vitamin receptor binding drug delivery conjugate intermediate described herein, the drug, or an analog or a derivative thereof, includes an alkylthiol nucleophile.

Additional examples of linkers, such as additional multivalent linkers, hydrophilic linkers, and the like are described in U.S. Patent Application Publication No. US 2005/0002942, U.S. Patent Application Publication No. US 2008/0248052, U.S. Patent Application Publication Serial No. US 2008/056824, and PCT International Application Publication No. WO 2009/002993, the disclosures of which are incorporated herein by reference in their entirety.

In another embodiment, a pharmaceutical composition comprising any one of the preceding targeted delivery conjugates and one or more carriers, excipients, diluents, and combinations thereof is described.

In another embodiment, a method is described for treating a pathogenic population of cells in a patient, the method comprising the step of administering an effective amount of any one of the preceding targeted delivery conjugates.

In another embodiment, a method for treating a patient in need of relief of a disease is described, the method comprising the step of administering an therapeutically effective amount of any one of the preceding targeted delivery conjugates to the patient. In one embodiment the disease is cancer.

The antifolate drug delivery conjugates described herein can be used for both human clinical medicine and veterinary applications. Thus, the host animal harboring the population of pathogenic cells and treated with the drug delivery conjugates can be human or, in the case of veterinary applications, can be a laboratory, agricultural, domestic, or wild animal. The methods described herein can be applied to host animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The methods are applicable to populations of pathogenic cells that cause a variety of pathologies in these host animals. The term pathogenic cells refers to for example cancer cells, infectious agents such as bacteria and viruses, bacteria- or virus-infected cells, and any other type of pathogenic cells that uniquely express, preferentially express, or over-express folate receptors. Pathogenic cells can also include any cells causing a disease state for which treatment with the antifolate drug delivery conjugates described herein results in reduction of the symptoms of the disease.

In another embodiment, the population of pathogenic cells can be a cancer cell population that is tumorigenic, including benign tumors and malignant tumors, or it can be non-tumorigenic. The cancer cell population can arise spontaneously or by such processes as mutations present in the germline of the host animal or somatic mutations, or it can be chemically-, virally-, or radiation-induced. The methods can be utilized to treat such cancers as carcinomas, sarcomas, lymphomas, Hodgkin's disease, melanomas, mesotheliomas, Burkitt's lymphoma, nasopharyngeal carcinomas, leukemias, and myelomas. The cancer cell population can include, but is not limited to, oral, thyroid, endocrine, skin, gastric, esophageal, laryngeal, pancreatic, colon, bladder, bone, ovarian, cervical, uterine, breast, testicular, prostate, rectal, kidney, liver, and lung cancers.

In embodiments where the pathogenic cell population is a cancer cell population, the effect of conjugate administration is a therapeutic response measured by reduction or elimination of tumor mass or of inhibition of tumor cell proliferation. In the case of a tumor, the elimination can be an elimination of cells of the primary tumor or of cells that have metastasized or are in the process of dissociating from the primary tumor. A prophylactic treatment with the drug delivery conjugate to prevent return of a tumor after its removal by any therapeutic approach including surgical removal of the tumor, radiation therapy, chemotherapy, or biological therapy is also described. The prophylactic treatment can be an initial treatment with the drug delivery conjugate, such as treatment in a multiple dose daily regimen, and/or can be an additional treatment or series of treatments after an interval of days or months following the initial treatment(s). Accordingly, elimination of any of the pathogenic cell populations treated using the described methods includes reduction in the number of pathogenic cells, inhibition of proliferation of pathogenic cells, a prophylactic treatment that prevents return of pathogenic cells, or a treatment of pathogenic cells that results in reduction of the symptoms of disease.

In cases where cancer cells are being eliminated, the methods can be used in combination with surgical removal of a tumor, radiation therapy, chemotherapy, or biological therapies such as other immunotherapies including, but not limited to, monoclonal antibody therapy, treatment with immunomodulatory agents, adoptive transfer of immune effector cells, treatment with hematopoietic growth factors, cytokines and vaccination.

In one embodiment, the antifolate drug delivery conjugates can be internalized into the targeted pathogenic cells upon binding of the antifolate moiety to a receptor, transporter, or other surface-presented protein that specifically binds the ligand and which is preferentially expressed on the pathogenic cells. Such internalization can occur, for example, through receptor-mediated endocytosis. Antifolate drug delivery conjugates containing one or more releasable linkers allow the binding ligand moiety and the drug to dissociate intracellularly and the drug can act on its intracellular target.

Generally, any manner of forming a conjugate between the bivalent linker (L) and the antifolate, or analog or derivative thereof, between the bivalent linker (L) and the drug, or analog or derivative thereof, including any intervening heteroatom, can be utilized. Also, any art-recognized method of forming a conjugate between the spacer linker, the releasable linker, and the any additional heteroatoms to form the linker L can be used. Covalent bonding can occur, for example, through the formation of amide, ester, disulfide, or imino bonds between acid, aldehyde, hydroxy, amino, sulfhydryl, or hydrazo groups present on any of the linkers, drugs, and/or antifolates.

In another illustrative aspect, any effective regimen for administering the antifolate drug delivery conjugates can be used. For example, the antifolate drug delivery conjugates can be administered as single doses, or can be divided and administered as a multiple-dose daily regimen. In other embodiments, a staggered regimen, for example, one to three days per week can be used as an alternative to daily treatment, and such intermittent or staggered daily regimen is considered to be equivalent to every day treatment and within the scope of the methods described herein. In one embodiment, the host is treated with multiple injections of the antifolate drug delivery conjugate to eliminate the population of pathogenic cells. In another embodiment, the host is injected multiple times (preferably about 2 up to about 50 times) with the antifolate drug delivery conjugate, for example, at 12-72 hour intervals or at 48-72 hour intervals.

In other embodiments, additional injections of the antifolate drug delivery conjugate can be administered to the patient at an interval of days or months after the initial injections(s) and the additional injections prevent recurrence of the disease state caused by the pathogenic cells.

In another embodiment, pharmaceutical compositions comprising an amount of a antifolate drug delivery conjugate effective to eliminate a population of pathogenic cells in a host animal when administered in one or more doses are described. The antifolate drug delivery conjugate is preferably administered to the host animal parenterally, e.g., intradermally, subcutaneously, intramuscularly, intraperitoneally, intravenously, or intrathecally. Alternatively, the antifolate drug delivery conjugate can be administered to the host animal by other medically useful processes, such as orally, and any effective dose and suitable therapeutic dosage form, including prolonged release dosage forms, can be used.

Examples of parenteral dosage forms include aqueous solutions of the active agent, in an isotonic saline, 5% glucose or other well-known pharmaceutically acceptable liquid carriers such as liquid alcohols, glycols, esters, and amides. The parenteral dosage form can be in the form of a reconstitutable lyophilizate comprising the dose of the drug delivery conjugate. In one aspect of the present embodiment, any of a number of prolonged release dosage forms known in the art can be administered such as, for example, the biodegradable carbohydrate matrices described in U.S. Pat. Nos. 4,713,249; 5,266,333; and 5,417,982, the disclosures of which are incorporated herein by reference, or, alternatively, a slow pump (e.g., an osmotic pump) can be used.

The unitary daily dosage of the antifolate drug delivery conjugate can vary significantly depending on the host condition, the disease state being treated, the molecular weight of the conjugate, its route of administration and tissue distribution, and the possibility of co-usage of other therapeutic treatments such as radiation therapy. The effective amount to be administered to a patient is based on body surface area, patient weight, and physician assessment of patient condition. In illustrative embodiments, effective doses can range, for example, from about 1 ng/kg to about 1 mg/kg, from about 1 µg/kg to about 500 µg/kg, and from about 1 µg/kg to about 100 µg/kg.

In one illustrative aspect, at least one additional composition comprising a therapeutic factor can be administered to the host in combination or as an adjuvant to the above-detailed methodology, to enhance the binding ligand drug delivery conjugate-mediated elimination of the population of pathogenic cells, or more than one additional therapeutic factor can be administered. The therapeutic factor can be selected from a chemotherapeutic agent, or another therapeutic factor capable of complementing the efficacy of the administered binding ligand drug delivery conjugate.

In one illustrative aspect, therapeutically effective combinations of these factors can be used. In one embodiment, for example, therapeutically effective amounts of the therapeutic factor, for example, in amounts ranging from about 0.1 MIU/m$^2$/dose/day to about 15 MIU/m$^2$/dose/day in a multiple dose daily regimen, or for example, in amounts ranging from about 0.1 MIU/m$^2$/dose/day to about 7.5 MIU/m$^2$/dose/day in a multiple dose daily regimen, can be used along with the antifolate drug delivery conjugates to eliminate, reduce, or neutralize pathogenic cells in a host animal harboring the pathogenic cells (MIU=million international units; m$^2$=approximate body surface area of an average human).

In another embodiment, chemotherapeutic agents, which are, for example, cytotoxic themselves or can work to enhance tumor permeability, are also suitable for use in the described methods in combination with the binding ligand drug delivery conjugates. Such chemotherapeutic agents include adrenocorticoids and corticosteroids, alkylating agents, antiandrogens, antiestrogens, androgens, aclamycin and aclamycin derivatives, estrogens, antimetabolites such as cytosine arabinoside, purine analogs, pyrimidine analogs, and methotrexate, busulfan, carboplatin, chlorambucil, cisplatin and other platinum compounds, tamoxiphen, taxol, paclitaxel, paclitaxel derivatives. Taxotere®, cyclophosphamide, daunomycin, rhizoxin, T2 toxin, plant alkaloids, prednisone, hydroxyurea, teniposide, mitomycins, discodermolides, microtubule inhibitors, epothilones, tubulysin, cyclopropyl benz[e]indolone, seco-cyclopropyl benz[e]indolone, O—Ac-seco-cyclopropyl benz[e]indolone, bleomycin and any other antibiotic, nitrogen mustards, nitrosureas, vincristine, vinblastine, and analogs and derivative thereof such as deacetylvinblastine monohydrazide, colchicine, colchicine derivatives, allocolchicine, thiocolchicine, trityl cysteine, Halicondrin B, dolastatins such as dolastatin 10, arnanitins such as α-amanitin, camptothecin, irinotecan, and other camptothecin derivatives thereof, geldanamycin and geldanamycin derivatives, estramustine, nocodazole, MAP4, colcemid, inflammatory and proinflammatory agents, peptide and peptidomimetic signal transduction inhibitors, and any other art-recognized drug or toxin. Other drugs that can be used include penicillins, cephalosporins, vancomycin, erythromycin, clindamycin, rifampin, chloramphenicol, aminoglycoside antibiotics, gentamicin, amphotericin B, acyclovir, trifluridine, ganciclovir, zidovudine, amantadine, ribavirin, maytansines and analogs and derivatives thereof, gemcitabine, and any other art-recognized antimicrobial compound.

The therapeutic factor can be administered to the host animal prior to, after, or at the same time as the binding ligand drug delivery conjugates and the therapeutic factor can be administered as part of the same composition containing the binding ligand drug delivery conjugate or as part of a different composition than the binding ligand drug delivery conjugate. Any such therapeutic composition containing the therapeutic factor at a therapeutically effective dose can be used.

The antifolate conjugates described herein can be prepared by art-recognized synthetic methods. The synthetic methods are chosen depending upon the selection of the optionally addition heteroatoms or the heteroatoms that are already present on the spacer linkers, releasable linkers, the drug, and/or or the antifolate. In general, the relevant bond forming reactions are described in Richard C. Larock. "Comprehensive Organic Transformations, a guide to functional group preparations," VCH Publishers, Inc. New York (1989), and in Theodora E. Greene & Peter G. M. Wuts, "Protective Groups ion Organic Synthesis," 2d edition, John Wiley & Sons, Inc. New York (1991), the disclosures of which are incorporated herein by reference. In another aspect, the antifolate is attached to the drug via a linker. In one embodiment, the linker includes an oligopeptide.

In another embodiment, the following illustrative antifolate-linker intermediate is prepared:

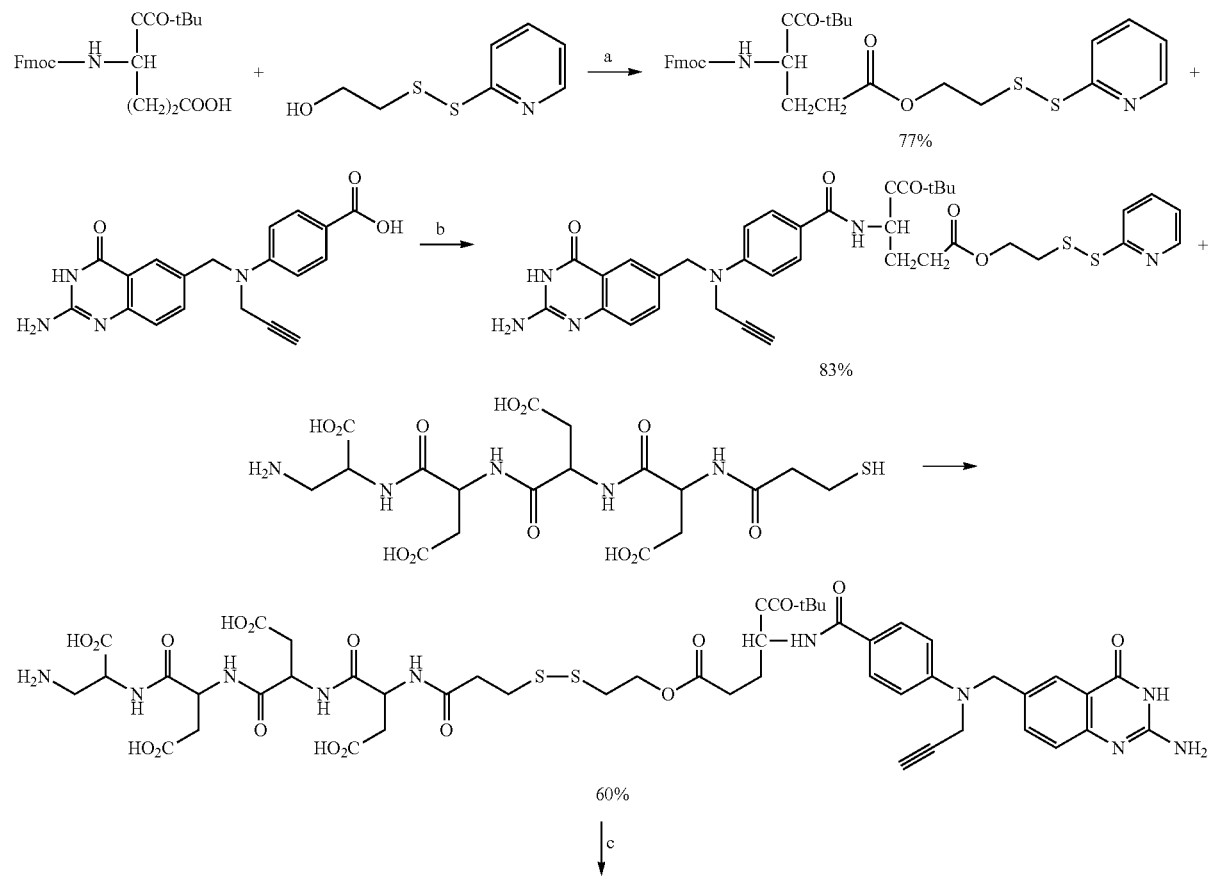

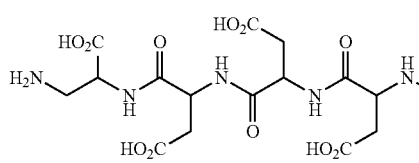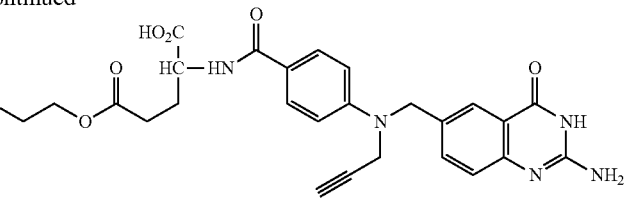

95% a) HOBt, DMAP, DCC; b) PyBop, DMAP, HOBt, Et₃N; c) TFA

It is to be understood that the foregoing process is illustrative and may be adapted and modified for the preparation of additional intermediates described herein.

EXAMPLES

The following illustrative examples are described.

Materials. Pteroic acid (Pte) and $N^{10}$-trifluoroacetylpteroic acid were prepared according to Xu et al., PCT International Application Serial No. PCT/US2006/009153, filed Mar. 14, 2006. Peptide synthesis reagents were purchased from NovaBiochem (La Jolla, Calif.) and Bachem (San Carlos, Calif.). Folate-free RPMI media (FFRPMI) and PBS were obtained from Gibco, Grand Island, N.Y. Bovine soluble milk folate binding protein (sFBP) was purchased from Scripps (item #F0524). $^3$H-thymidine was purchased from Moravek Biochemicals, Brea, Calif. All other common reagents were purchased from Sigma (St. Louis, Mo.) or other major suppliers.

Comparative compounds EC20, EC119, EC17, EC72, EC140 and EC145 were obtained from Endocyte, Inc. (West Lafayette, Ind.). Their syntheses, purifications and analytical characterizations have been described in detail elsewhere (Leamon et al. Bioconjugate Chemistry 2002; 13(6):1200-10; Lu et al. Cancer Immunol Immunother 2002; 51(3):153-62; Leamon et al. Bioconjug Chem 2005:16(4):803-11; Leamon et al. Bioconjug Chem 2006; 17(5): 1226-32; Vlahov et al. Bioorg Med Chem Lett 2006; 16(19):5093-6). Comparative example des-glutamyl CB3717 and antifolate CB3717 may also be prepared according to known procedures (Jones et al. Eur J Cancer 1981; 17(1):11-9; Jones et al. J Med Chem 1986; 29(6):1114-8).

Comparative Example

Synthesis of EC216. In a dry 10 mL round bottom flask, Pte-Cys-OH (7.6 ing, 18.3 μmol) and 3-(4-desacetylvinblastinyl)hydrazinecarboxylic acid 2-pyridyldithioethyl ester (15 mg, 15.3 μM) were dissolved in 0.8 mL of DMSO under argon atmosphere. DIPEA (54 μL, 0.31 mM, 20 equiv.) was added to the above solution, and the resulting clear solution was stirred under argon for 3 h. Progress of the reaction was monitored by analytical HPLC (10 mM ammonium acetate, pH=7.0 and acetonitrile). The reaction mixture was filtered and injected on a prep-HPLC column (Waters XTerra C18, 7 μm, 19×300 mm). Elution with 1 mM sodium phosphate buffer, pH=7.0 (A), and acetonitrile (B) (method: 1% B to 80% B in 30 minutes at 15 mL/min) yielded pure fractions containing the product. Pure fractions were combined and acetonitrile was removed under reduced pressure at ambient temperature. The resulting EC216 conjugate was isolated after freeze-drying for 48 h (10 mg, 51%). $^1$H NMR (300 MHz, DMSO-$d_6$, with $D_2O$) δ 8.63 (s, 1H), 7.58 (d, J=8.7 Hz, 2H), 7.36 (d, J=8.4 Hz, 1H), 7.24 (d, J=8.1 Hz, 1H), 7.10-6.80 (m, 2H), 6.65 (d, J=9.0 Hz, 2H), 6.41 (s, 1H), 6.19 (s, 1H), 5.68 (m, 1H), 5.56 (d, J=10.2 Hz, 1H), 4.46 (s, 2H), 4.35-3.90 (m, 4H), 3.69 (s, 3H), 3.45-2.20 (m, 23H), 2.05-1.85 (m, 2H), 1.56 (m, 2H), 1.40-0.95 (m, 8H), 0.78 (t, J=7.5 Hz, 3H), 0.71 (t, J=7.2 Hz, 3H); LCMS (ESI): (M+H)+=1286.34.

Synthesis of α-t-Butyl-γ-2-(Pyridyl)disulfide-ethyl-L-glutamic diester EC0614

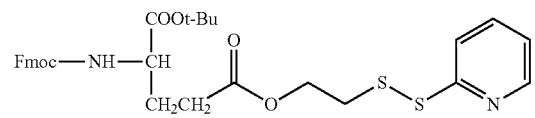

Fmoc α-(t-butyl)-L-glutamic acid (1.275 g, 3 mmole), 2-(2-pyridyldithio)ethanol (684 mg, 3.0 mmole), DMAP (806 mg, 6.6 mmole) HOBt (450 mg, 3.0 mmole) was dissolved in 150 mL $CH_2Cl_2$. To the solution was added DCC (680 mg, 3.3 mmole), the solution was stirred at room temperature under argon overnight. The reaction mixture was filtered and the solvent was evaporated. Toluene was added to dissolve the desired product and then more $CH_2Cl_2$, the organic solution was washed by NaOAc (0.1M)/10% NaCl (pH=6), then dried over $MgSO_4$, filtered and evaporated to give a clear oil. The crude product was put on silica column with 50% EtOAc/50% petroleum ether as eluents to give 1.5 g of product. $^1$H NMR ($CDCl_3$) 8.47-8.44 (m, 1H), 7.46 (d, J=7.4 Hz, 2H), 7.68-7.58 (m, 4H), 7.39-7.26 (m, 4H), 7.10-7.05 (m, 1H), 5.42 (d, J=8.0 Hz, 1H), 4.40-4.26 (m, 4H), 4.22 (t, J=7.2 Hz, 1H), 3.03 (s, t, J=6.3 Hz, 2H), 2.50-2.30 (m, 2H), 2.28-2.18 (m, 1H), 2.02-1.85 (m, 1H), 1.48 (s, 9H). $^{13}$C NMR ($CDCl_3$) 172.7, 171.2, 159.8, 156.2, 149.9, 144.1, 143.9, 141.5, 137.26, 127.9, 127.3, 125.3, 121.1, 120.2, 120.1, 82.8, 67.3, 62.6, 53.9, 47.4, 37.4, 30.3, 28.2, 28.1

Synthesis of EC282 (CB3717)

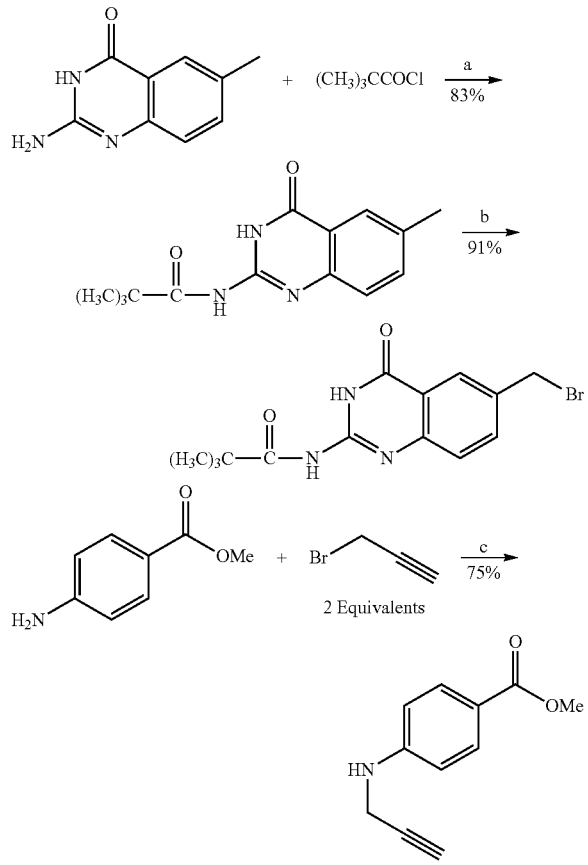

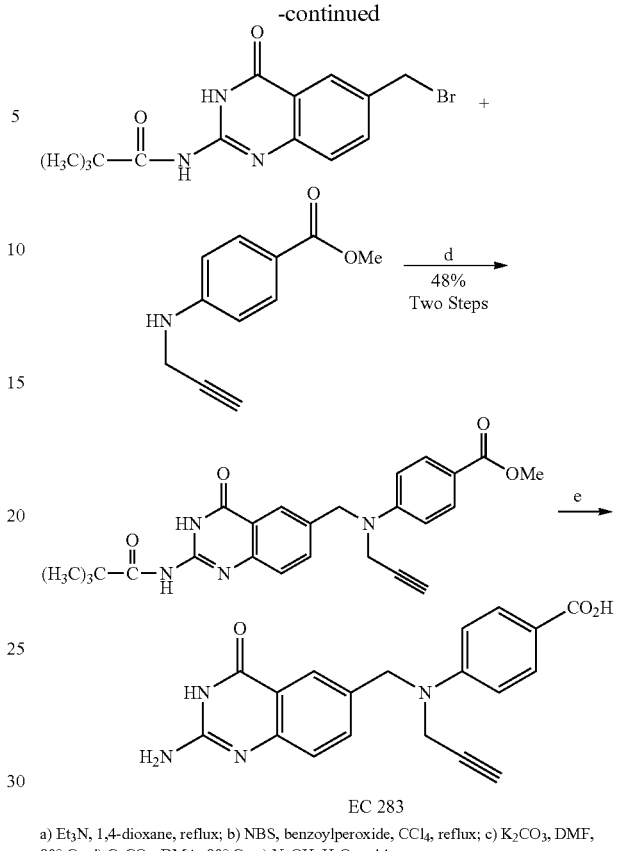

a) Et$_3$N, 1,4-dioxane, reflux; b) NBS, benzoylperoxide, CCl$_4$, reflux; c) K$_2$CO$_3$, DMF, 80° C.; d) CaCO$_3$, DMA, 80° C.; e) NaOH, H$_2$O, >4 hours.

Synthesis of N$^{10}$-Propargyl-5,8-dideazefolic α-t-Butyl-γ-2-(pyridyl)disulfide-ethyl-diester EC0615

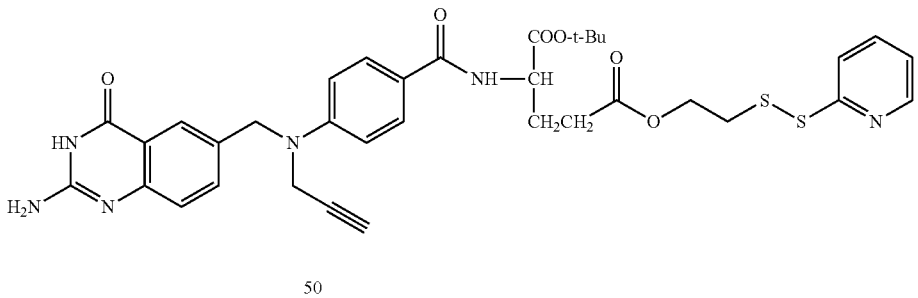

614 mg of Fmoc protected glutamic acid EC0614 was dissolved in 12.0 mL DMF, 5,8-dideazapteroic acid (350 mg), PyBOP (510 mg) HOBt (150 mg), DMAP (135 mg) were added to the solution. The reaction mixture was then stirred for 5 mins, 0.3 mL Et$_3$N was added and the reaction mixture was stirred overnight. The reaction mixture was added to NaOAc (0.1M)/10% NaCl (pH=6), centrifuged and got the crude product 601 mg, the crude product was purified by HPLC (10 mM NH$_4$OAc, pH=5.2 and acetonitrile) to give 360 mg product. $^1$H NMR (DMSO-d6) 10.92 (br, 1H, lactam NH), 8.42 (dd, J=4.8, 1.0 Hz, 1H), 8.23 (d, J=8.7 Hz, 1H), 7.82-7.70 (m, 5H), 7.47 (dd, J=8.3, 2.1 Hz, 1H), 7.20 (m, 1H), 7.13 (d, J=8.7 Hz, 1H), 6.83 (d, J=8.8 Hz, 2H), 6.28 (br, 2H), 4.64 (s, 2H), 4.32-4.19 (m, 5H), 3.19 (t, J=2.2 Hz, 1H), 3.07 (t, J=6.0 Hz, 2H), 2.37 (t, J=7.5 Hz, 2H), 2.10-1.83 (m, 2H), 1.37 (s, 9H)

Synthesis Of Desacetylvinblastine Hydrazide Derivative EC0616

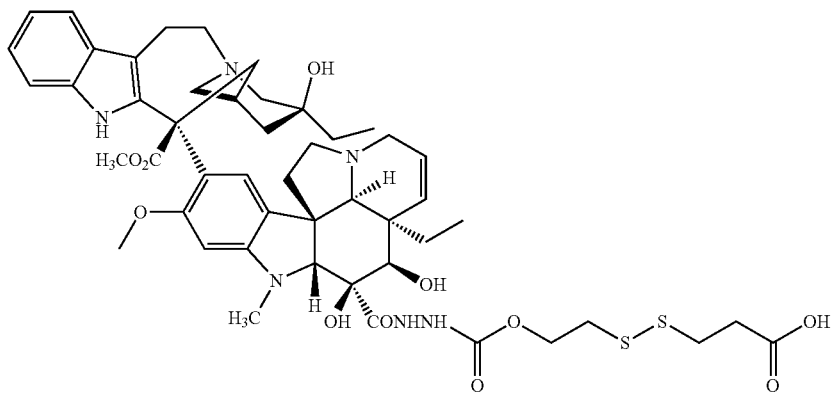

39.5 mg of DAVLBH pyridyl disulfide derivative was dissolved in 0.5 mL THF/0.5 mL H₂O, 4.2 mg of mercaptopropionic acid was dissolved in 0.5 mL THF/0.5 mL H₂O, the solution was adjusted to pH 7 while purged with argon. Mercaptopropionic acid solution was added to vinblastine solution and stirred for 20 mins. The reaction mixture was purified on HPLC (10 mM NH₄OAc, pH 5.2), 24 mg of product was obtained after lyophilization. LCMS (ESI) 977.38; $^1$H NMR (DMSO-d6) 9.39 (s, br, 1H), 9.29 (s, br, 1H), 9.12 (s, br, 1H), 8.61 (s, br, 1H), 7.35 (d, J=8.0 Hz, 1H), 7.24 (d, J=8.0 Hz, 1H), 6.99 (t, J=7.0 Hz, 1H), 6.90 (t, J=7.0 Hz, 1H), 6.40 (s, 1H), 6.18 (s, 1H), 5.67 (dd, J=10.6, 4.7 Hz, 1H), 5.56 (d, J=10.6 Hz, 1H), 4.21 (t, br, 2H), 4.14-3.90 (nm, 3H), 3.78 (s, 1H), 3.70 (s, 3H), 3.50 (s, 3H), 3.38 (s, 2H), 3.26-3.00 (m, 6H), 3.00-2.87 (m, 5H), 2.86 (s, 1H), 2.76 (s, 3H), 2.71-2.57 (m, 2H), 2.52-2.47 (m, 3H), 2.40-2.38 (m, 2H), 2.05-1.88 (m, 2H), 1.70-1.50 (m, 2H), 1.38-1.20 (m, 5H), 0.88-0.56 (m, 7H)

Synthesis Of EC0285

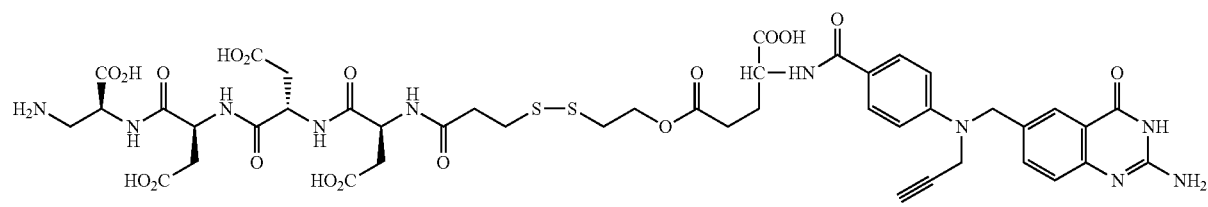 [SMILES: C#CCN(Cc1ccc2nc(N)[nH]c(=O)c2c1)c1ccc(C(=O)NC(CCC(=O)OCCSSCCC(=O)N[C@@H](CC(=O)O)C(=O)N[C@@H](CC(=O)O)C(=O)N[C@@H](CC(=O)O)C(=O)N[C@@H](CN)C(=O)O)C(=O)O)cc1]

117 mg of EC0615 and 87 mg of thiopeptide in 6.0 mL DMSO, purged with argon, added 0.2 mL DIPEA, after 2 hours, HPLC purification (10 mM NH₄OAc, pH 5.2/acetonitrile) gave 126 mg of product, 90 mg of the product was dissolved in 5 mL TFA/TIPS (97.5:2.5) and stirred for 1 hour. Then the reaction mixture was added to cold Et₂O, and stirred for 10 min. The precipitate was centrifuged and washed with Et₂O three times. The reaction afforded 82 mg of white solid. LCMS (ESI) 1073.30; $^1$H NMR (D₂O) 7.57 (s, 1H), 7.48 (d, J=9.0 Hz, 2H), 7.22 (d, J=8.4 Hz, 1H), 6.88 (d, J=8.7 Hz, 1H), 6.60 (d, J=9.0 Hz, 2H), 4.52-4.43 (m, 3H), 4.36-4.30 (m, 2H), 4.22 (q, J=4.5 Hz, 1H), 3.98 (s, br, 2H), J=4.5 Hz, 1H), 3.88-3.73 (m, 2H), 3.28 (dd, J=14, 9 Hz, 1H), 3.11 (t, dd, J=14, 9 Hz, 1H), 2.70-2.48 (m, 8H), 2.45-2.31 (m, 6H), 2.28-2.20 (m, 2H), 2.17-2.03 (m, 2H), 1.96-1.82 (m, 2H). $^{13}$C NMR (D₂O) 181.6, 178.5, 178.2, 177.9, 177.8, 175.7, 174.2, 173.5, 168.9, 154.1, 150.2, 141.7, 133.9, 122.9, 128.9, 124.6, 121.2, 118.7, 115.8, 112.9, 80.1, 73.5, 63.1, 54.9, 54.2, 52.4, 51.7, 41.1, 38.8, 38.7, 38.4, 35.9, 34.8, 33.2, 30.9, 30.8, 27.1, 23.3.

Synthesis of EC0284

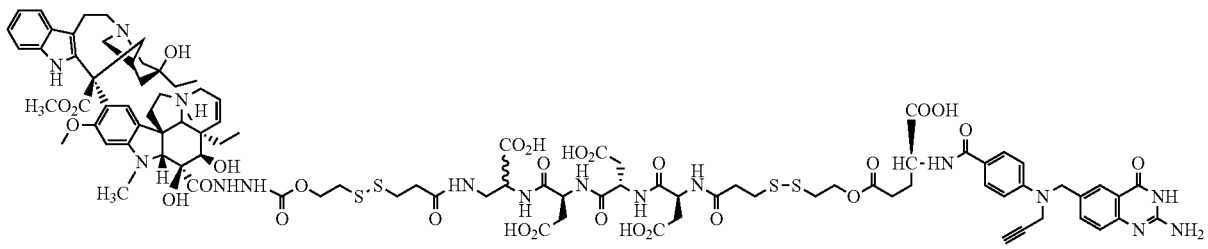

22.0 mg of EC0616 in 0.1 mL THF, was added 2.6 mg NHS in 0.1 mL THF, 2.7 mg DIPEA in 0.1 mL THF, 11.7 mg of PyBOP in 0.1 mL DMF. The reaction mixture was stirred at room temperature for 40 mins with HPLC monitoring the reaction. Another equivalent of NHS, DIPEA. PyBOP was added to the reaction and stirred for 40 mins, 16.0 mg of EC0285 was dissolved in 0.5 mL $H_2O$, then adjusted to pH 7.5 by $NaHCO_3$ aqueous solution, then mixed with the above reaction solutions. After 1/2 h, HPLC purification with 1 mM phosphate buffer (pH 7) gave 11.2 mg of EC0284 after Lyophilization. LCMS (ESI) (M+H)$^+$2033.4; $^1$H NMR (DMSO-d6+$D_2O$) 7.57 (s, 1H), 7.62 (d, J=8.4 Hz, 2H), 7.46 (d, J=8.7 Hz, 1H), 7.34 (d, J=7.8 Hz, 1H), 7.23 (d, J=7.8 Hz, 1H), 7.14 (d, J=8.4 Hz, 1H), 6.98 (t, J=7.5 Hz, 1H), 6.90 (t, J=7.5 Hz, 1H), 6.82 (d, J=8.7 Hz, 2H), 6.40 (s, 1H), 6.18 (s, 1H), 5.67 (dd, 1H), 5.56 (dd, 1H), 4.62 (s, br, 2H), 4.51 (t, J=6.3 Hz, 1H), 4.36-4.26 (m, 4H), 4.18 (m, 2H), 4.14-3.96 (m, 5H), 3.76 (s, 1H), 3.69 (s, 2H), 3.26-2.65 (m, 32H), 2.36-1.83 (m, 18H), 1.71 (m, 6H), 1.64-1.38 (m, 5H), 1.32-1.13 (m, 13H), 0.88-0.56 (m, 11H).

Synthesis of α-t-Butyl-γ-2-(Pyridyl)disulfide-ethyl Methotrexate EC0619

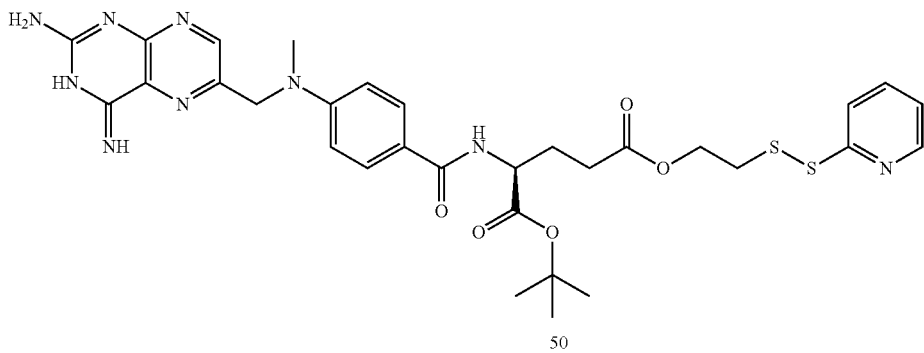

To a well stirred solution of pyridyldithio-derivative of glutamic acid EC0614 (50 mg, 1 eq.) in dry DMF was added 4-[N-(2,4-diamino-6-pteridinylmethyl)-N-methylamino] benzoic acid (30 mg, 1 eq.). PyBop (48 mg, 1.1 eq.), 1-hydroxybenzotriazole (12 mg, 1.1 eq.) and 4-(dimethyl-amino)pyridine (11 mg, 1.1 eq.) were added. After stirring for 5 min, triethylamine (35 μL, 3 eq.) was added. The reaction mixture was allowed to stir at room temperature for 18 h (TLC, 20% MeOH in $CH_2Cl_2$). The solvent was removed under reduced pressure. The α-t-butyl-γ-2-(pyridyl)disulfide-ethyl methotrexate (38 mg) was purified by preparative HPLC (10 mM ammonium acetate, pH=7 and acetonitrile). ESI-MS: (M+H)$^+$=680.31; $^1$H NMR (300 MHz, DMSO-d$_6$): δ 8.55 (s, 1H), 8.41 (dd, 1H), 8.19 (d, 1H), 7.77 (m, 1H), 7.70 (d, 2H), 7.19 (m, 1H), 6.80 (d, 2H), 4.76 (s, 2H), 4.28 (m, 1H), 4.20 (t, 2H), 3.19 (s, 3H), 3.06 (t, 2H), 2.36 (t, 2H), 1.97 (m, 2H), 1.37 (s, 9H).

Synthesis of γ-2-(Pyridyl)disulfide-ethyl Methotrexate EC0620

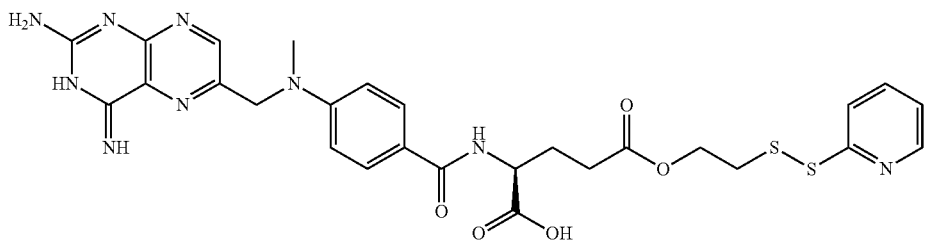 [SMILES: CN(Cc1cnc2nc(N)[nH]c(=N)c2n1)c1ccc(C(=O)N[C@@H](CCC(=O)OCCSSc2ccccn2)C(=O)O)cc1]

α-t-Butyl-γ-2-(pyridyl)disulfide-ethyl methotrexate EC0619 (20 mg) was dissolved in 0.5 mL TFA/TIPS solution (97.5% TFA, 2.5% TIPS). The reaction mixture was stirred for 1 h (analytical HPLC, 10 mM NH$_4$OAc, pH=7 and acetonitrile), then precipitated in diethyl ether. The resulting precipitate was washed with diethyl ether (3×), isolated by centrifugation, and dried under vacuum to afford the crude product (18 mg). This yellow powder, γ-2-(pyridyl)disulfide-ethyl methotrexate, was used in the next step without further purification. ESI-MS: (M+H)$^+$=624.32; $^1$H NMR (300 MHz, DMSO-d$_6$): δ 12.58 (br, 1H), 8.69 (s, 1H), 8.41 (m, 1H), 8.23 (d, 1H), 7.76 (m, 1H), 7.70 (d, 2H), 7.19 (m, 1H), 6.80 (d, 2H), 4.85 (s, 2H), 4.35 (m, 1H), 4.19 (t, 2H), 3.23 (s, 3H), 3.05 (t, 2H), 2.35 (t, 2H), 2.08 (m, 1H), 1.91 (m, 1H).

Synthesis of EC0401

Fmoc-Glu-O$^t$Bu (30 mg, 1 eq.) was dissolved in dry EtOAc. The solution was cooled to −15° C. With stirring under argon, N,N-diisopropylethylamine (26 μL, 2.1 eq.) and isobutyl chloroformate (14 μL, 1.5 eq.) were added to this solution. After stirring at −15° C. for 45 min, hydrazinecarboxylic acid 2-(pyridin-2-yl-dislfanly) ethyl ester (24 mg, 1.4 eq.) was added. The reaction mixture is stirred at −15° C. for 30 min, and then it was allowed to warm to room temperature within 5 min. The stirring was continued for an additional 30 min at room temperature (TLC, 5% MeOH in CH$_2$Cl$_2$). The solvent was evaporated to dryness. The resulting pyridyldithio-derivative of glutamic acid EC0401 (40 mg) was purified on a silica gel column (66% EtOAc in pet. ether). ESI-MS: (M+H)$^+$=653.1; $^1$H NMR (CDCl$_3$ & CD$_3$OD) δ 8.48 (d, 1H), 7.73 (m, 4H), 7.58 (d, 2H), 7.37 (t, 2H), 7.28 (t, 2H), 7.14 (m, 1H), 5.76 (m, 1H), 4.35 (t, 2H), 4.32 (t, 2H), 4.18 (t, 1H), 3.01 (t, 2H), 2.24 (m, 4H), 1.90 (m, 1H), 1.43 (s, 9H).

Synthesis of Methotrexate-O$^t$Bu-Hydrazide Pyridyldisulfide-ethanol Carbazate EC0402

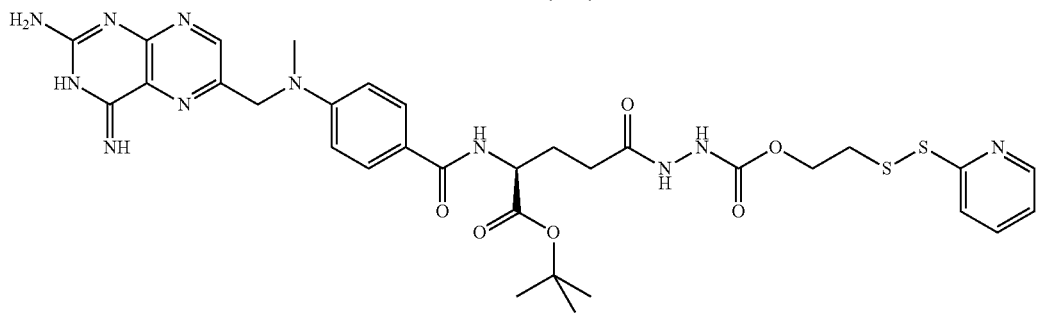

To a well stirred solution of pyridyldithio-derivative of glutamic acid EC0401 (45 mg, 1 eq.) in dry DMF was added 4-[N-(2,4-diamino-6-pteridinylmethyl)-N-methylamino]benzoic acid (25 mg, 1 eq.) followed by PyBop (39 mg, 1.1 eq.), 1-hydroxybenzotriazole (10 mg, 1.1 eq.), and 4-(dimethylamino)pyridine (9 mg, 1.1 eq.). After 5 min of stirring, triethylamine (29 μL, 3 eq.) was added. The reaction mixture was allowed to stir at room temperature for 18 h. The solvent was removed under reduced pressure. The t-butyl-protected pyridyldithio-derivative of methotrexate EC0402 (25 mg) was purified by preparative HPLC (10 mM NH$_4$OAc, pH=7 and acetonitrile). ESI-MS: (M+H)$^+$=738.1: $^1$H NMR (DMSO-d6 & D$_2$O) δ 8.57 (s, 1H), 8.46 (d, 1H), 7.80 (m, 2H), 7.73 (d, 2H), 7.24 (t, 1H), 6.81 (d, 2H), 4.79 (s, 2H), 4.22 (m, 1H), 4.20 (t, 2H), 3.21 (s, 3H), 3.09 (t, 2H), 2.21 (t, 2H), 2.01 (m, 1H), 1.91 (m, 1H), 1.39 (s, 9H).

Synthesis of Methotrexate Hydrazide Pyridyldisulfide-ethanol Carbazate EC0403

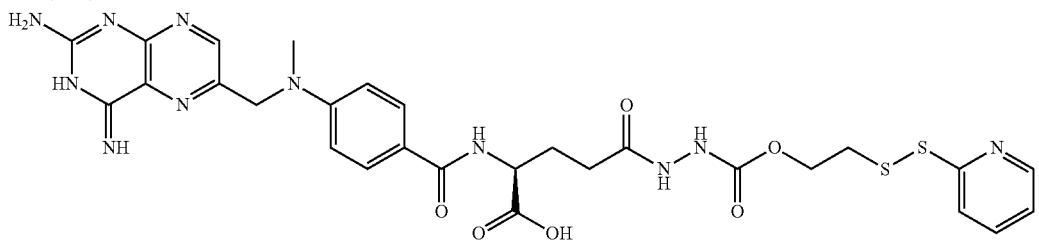 [SMILES: CN(Cc1cnc2nc(N)[nH]c(=N)c2n1)c1ccc(C(=O)N[C@@H](CCC(=O)NNC(=O)OCCSSc2ccccn2)C(=O)O)cc1]

The t-butyl-protected pyridyldithio-derivative of methotrexate EC0402 (25 mg) was dissolved in 0.5 mL of TFA/TIPS solution (97.5% TFA, 2.5% TIPS). The reaction mixture was stirred for 0.5 h then precipitated in diethyl ether (analytical HPLC, 10 mM NH$_4$OAc, pH=7 and acetonitrile). The resulting precipitate was washed with diethyl ether (3×), isolated by centrifugation, and dried under vacuum to afford the crude product (18 mg). This yellow powder, methotrexate hydrazide pyridyldisulfide-ethanol carbazate EC0403, was used in the next step without further purification. ESI-MS: (M+H)$^+$=682.3; $^1$H NMR (DMSO-d6 & D$_2$O) δ 8.70 (s, 1H), 8.44 (d, 1H), 7.82 (m, 2H), 7.74 (d, 2H), 7.24 (t, 1H), 6.81 (d, 2H), 4.87 (s, 2H), 4.32 (dd, 1H), 4.20 (t, 2H), 3.24 (s, 3H), 3.08 (t, 2H), 2.21 (t, 2H), 2.05 (m, 1H), 1.94 (m, 1H).

Synthesis of α-t-Butyl-γ-2-(pyridyl)disulfide-ethyl Aminopterin EC0459

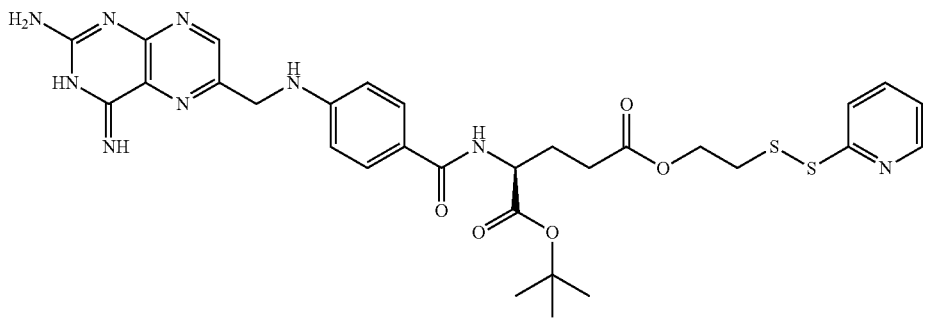 [SMILES: CC(C)(C)OC(=O)[C@H](CCC(=O)OCCSSc1ccccn1)NC(=O)c1ccc(NCc2cnc3nc(N)[nH]c(=N)c3n2)cc1]

To a well stirred solution of pyridyldithio-derivative of glutamic acid (95 mg, 1 eq.) in 1 mL dry DMF was added Des-glu-aminopterin (50 mg, 1 eq.). PyBop (94 mg, 1.1 eq.), 1-hydroxybenzotriazole (24 mg, 1.1 eq.) and 4-(dimethylamino)pyridine (22 mg, 1.1 eq.) were added. After stirring for 5 min, triethylamine (67 μL, 3 eq.) was added. The reaction mixture was allowed to stir at room temperature overnight (TLC, 20% MeOH in CH$_2$Cl$_2$). The solvent was removed under reduced pressure. The -t-butyl--2-(pyridyl)disulfide-ethyl methotrexate (45 mg) was purified by preparative HPLC (10 mM ammonium acetate, pH=7 and acetonitrile). ESI-MS: (M+H)$^+$=666.2; $^1$H NMR (300 MHz, DMSO-d$_6$): δ 8.69 (s, 1H), 8.42 (m, 1H), 8.19 (d, J=7.7 Hz, 1H), 7.77 (m, 1H), 7.70 (d, J=8.8 Hz, 2H), 7.20 (m, 1H), 6.74 (d, J=8.8 Hz, 2H), 4.49 (s, 2H), 4.28 (m, 1H), 4.22 (t, J=6.0 Hz, 2H), 3.07 (t, J=6.0 Hz 2H), 2.38 (t, J=7.7 Hz 2H), 2.07-1.82 (m, 2H), 1.37 (s, 9H).

Synthesis of γ-2-(Pyridyl)disulfide-ethyl Aminopterin EC0460

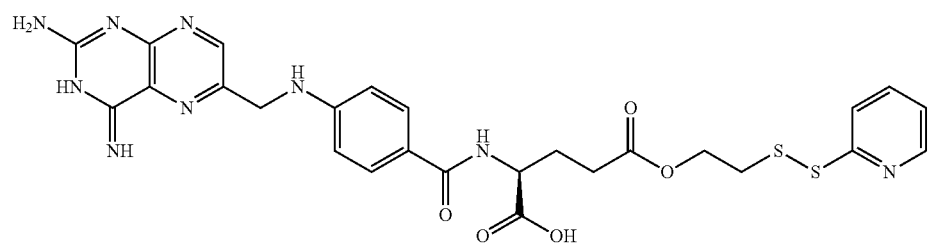 [SMILES: N=c1[nH]c(N)nc2ncc(CNc3ccc(C(=O)N[C@@H](CCC(=O)OCCSSc4ccccn4)C(=O)O)cc3)nc12]

α-t-Butyl-γ-2-(pyridyl)disulfide-ethyl aminopterin EC0459 (36 mg) was dissolved in 0.5 mL TFA/TIPS solution (97.5% TFA, 2.5% TIPS). The reaction mixture was stirred for 1 h (analytical HPLC, 10 mM NH$_4$OAc, pH=7 and acetonitrile), then precipitated in diethyl ether. The resulting precipitate was washed with diethyl ether (3×), isolated by centrifugation, and dried under vacuum to afford the crude product (30 mg). This yellow powder, γ-2-(pyridyl)disulfide-ethyl aminopterin, was used in the next step without further purification. ESI-MS: (M+H)$^+$=610.1; $^1$H NMR (300 MHz, DMSO-d$_6$+D$_2$O): δ 8.81 (s, 1H), 8.42 (m, 1H), 7.78 (m, 1H), 7.72 (dd, J=8.5 Hz, 2H), 7.20 (m, 1H), 6.74 (d, J=8.5 Hz, 2H), 4.60 (s, 2H), 4.36 (q, J=5.0 Hz, 1H), 3.06 (t, J=6.1 Hz, 2H), 2.37 (t, J=7.6 Hz, 2H), 2.15-2.01 (m, 1H), 2.00-1.86 (m, 1H).

Synthesis of Aminopterin-O-t-butyl-hydrazide Pyridyldisulfide-ethanol Carbazate EC0468

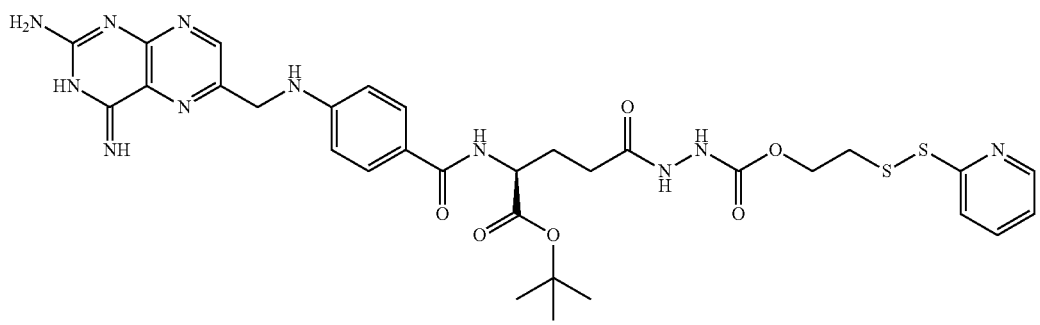 [SMILES: CC(C)(C)OC(=O)[C@H](CCC(=O)NNC(=O)OCCSSc1ccccn1)NC(=O)c1ccc(NCc2cnc3nc(N)[nH]c(=N)c3n2)cc1]

To a well stirred solution of pyridyldithio-derivative of glutamic acid EC0401 (104 mg, 1 eq.) in 1 mL dry DMF was added Des-glu-aminopterin (50 mg, 1 eq.) followed by PyBop (94 mg, 1.1 eq.), 1-hydroxybenzotriazole (24 mg, 1.1 eq.), and 4-(dimethylamino)pyridine (22 mg, 1.1 eq.). After 5 min of stirring, triethylamine (67 μL, 3 eq.) was added. The reaction mixture was allowed to stir at room temperature for overnight. The solvent was removed under reduced pressure. The t-butyl-protected pyridyldithio-derivative of methotrexate EC0468 (68 mg) was purified by preparative HPLC (10 mM NH$_4$OAc, pH=7 and acetonitrile). ESI-MS: (M+H)$^+$=724.2: $^1$H NMR (DMSO-d6 & D$_2$O) δ 8.69 (s, 1H), 8.45 (d, J=4.5 Hz, 1H), 7.86-7.74 (m, 2H), 7.70 (d, J=8.8 Hz, 2H), 7.24 (t, J=6.2 Hz, 1H), 6.73 (d, J=8.8 Hz, 2H), 4.49 (s, 2H), 4.27-4.18 (m, 1H), 3.08 (t, J=6.2 Hz, 2H), 3.03-2.97 (m, 2H), 2.22 (t, J=7.6 Hz, 2H), 2.08-1.86 (m, 4H), 1.39 (s, 9H).

Synthesis of Aminopterin Hydrazide Pyridyldisulfide-ethanol Carbazate EC0469

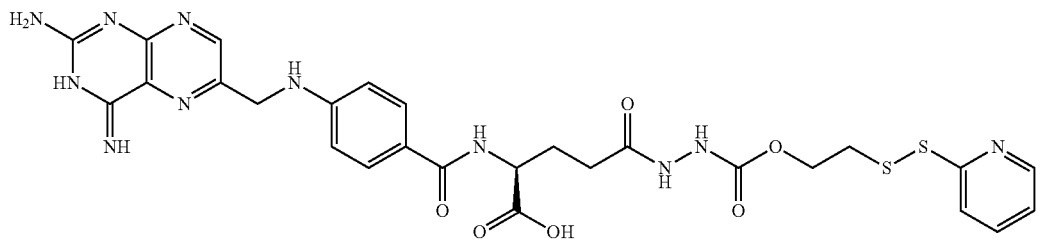 [SMILES: N=c1[nH]c(N)nc2ncc(CNc3ccc(C(=O)N[C@@H](CCC(=O)NNC(=O)OCCSSc4ccccn4)C(=O)O)cc3)nc12]

The t-butyl-protected pyridyldithio-derivative of aminopterin EC0468 (33 mg) was dissolved in 0.5 mL of TFA/TIPS solution (97.5% TFA, 2.5% TIPS). The reaction mixture was stirred for 0.5 h then precipitated in diethyl ether (analytical HPLC, 10 mM NH$_4$OAc, pH=7 and acetonitrile). The resulting precipitate was washed with diethyl ether (3×), isolated by centrifugation, and dried under vacuum to afford the crude product (30 mg). This yellow powder, methotrexate hydrazide pyridyldisulfide-ethanol carbazate EC0469, was used in the next step without further purification. ESI-MS: (M+H)$^+$=668.2; $^1$H NMR (DMSO-d6 & D$_2$O) δ 8.82 (s, 1H), 8.44 (d, J=4.7 Hz, 1H), 7.80 (m, 2H), 7.71 (d, J=8.8 Hz, 2H), 7.24 (t, J=4.6 Hz, 1H), 6.74 (d, J=8.8 Hz, 2H), 4.60 (s, 2H), 4.32 (dd, J=5.0 Hz, 1H), 4.20 (t, J=6.0 Hz, 2H), 3.07 (t, J=6.0 Hz, 2H), 2.22 (t, J=7.8 Hz, 2H), 2.15-1.94 (m, 2H).

It is to be understood that foregoing processes may be adapted with the appropriate selection of starting materials to prepare additional conjugates described herein, such as the following:

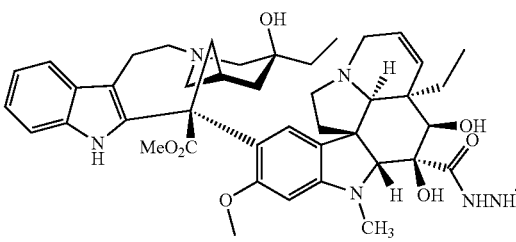
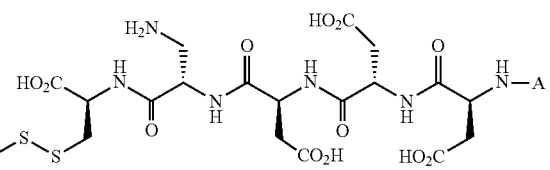

wherein A is N$^9$—CH$_3$-5-d(i)PteGlu, 5-d(i)PteGlu, IAHQ, BW1843U89, 2-NH$_2$-ZD1694, ZD1694, CB3717, 5-dH$_4$PteAPBA, 5-dPteHCysA, or DDATHF.

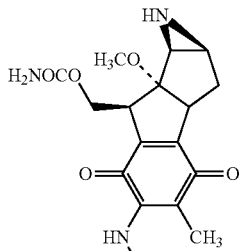

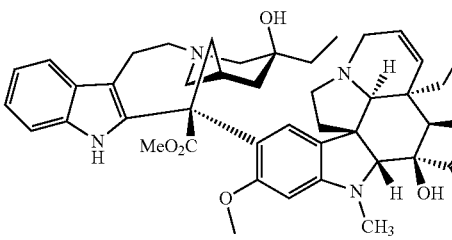
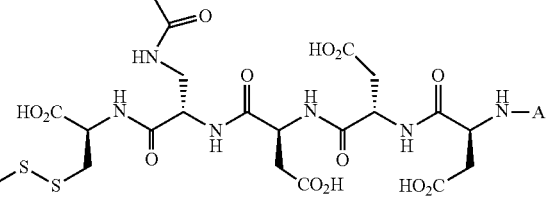

wherein A is N$^9$—CH$_3$-5-d(i)PteGlu, 5-d(i)PteGlu, IAHQ, BW1843U89, 2-NH$_2$-ZD1694, ZD1694, CB3717, 5-dH$_4$PteAPBA, 5-dPteHCysA, or DDATHF.

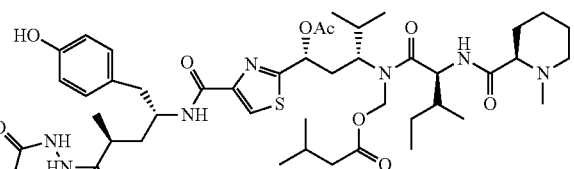
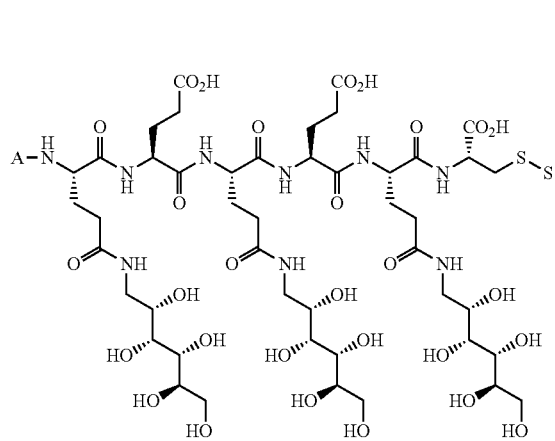
wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.
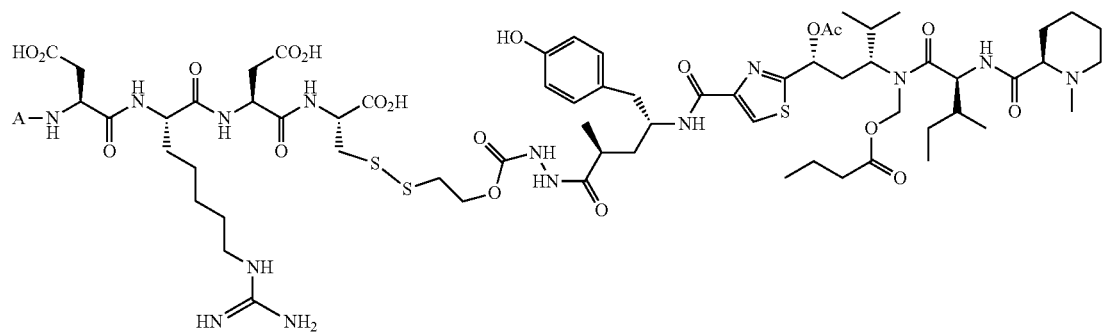
wherein A is N⁹—CH₃-5d(i)PteGlu, 5-d(i)PteGlu, IAHQ, BW1843U89, 2-NH₂-ZD1694, ZD1694, CR3717, 5-dH₄PteAPBA, 5-dPteHCysA, or DDATHF.
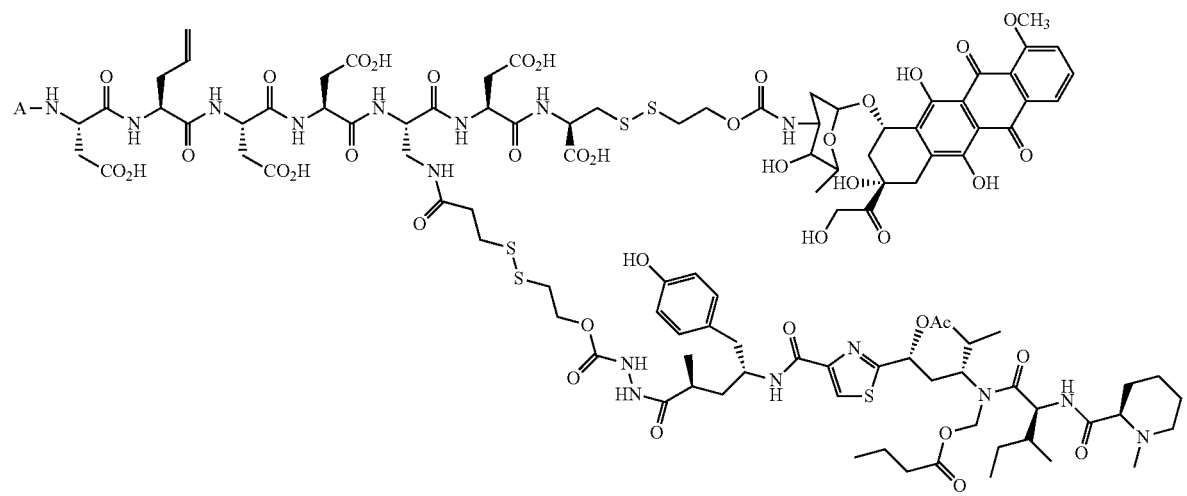
wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.

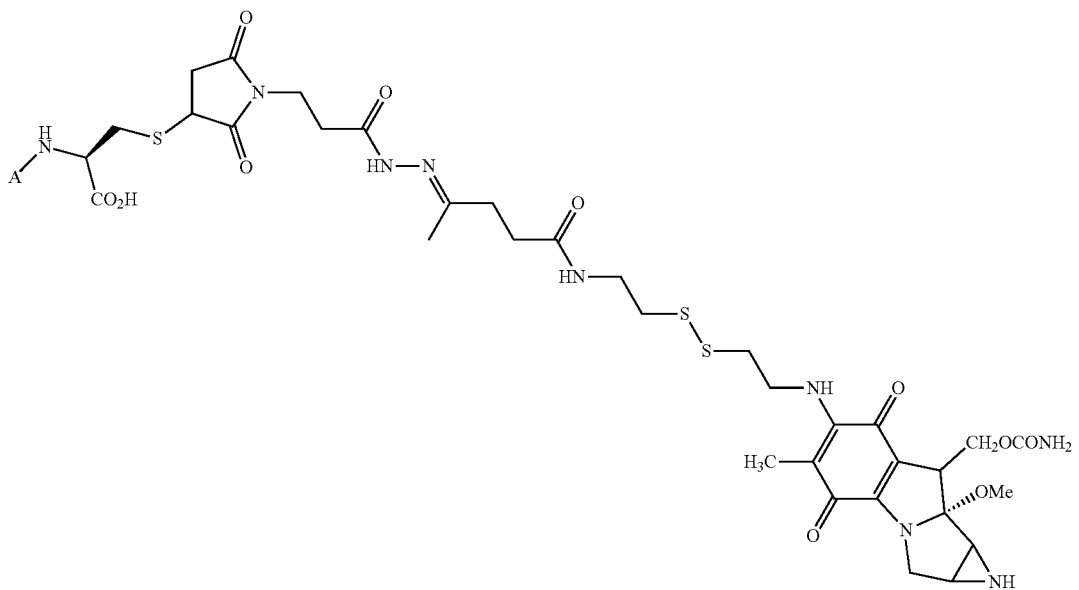
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.
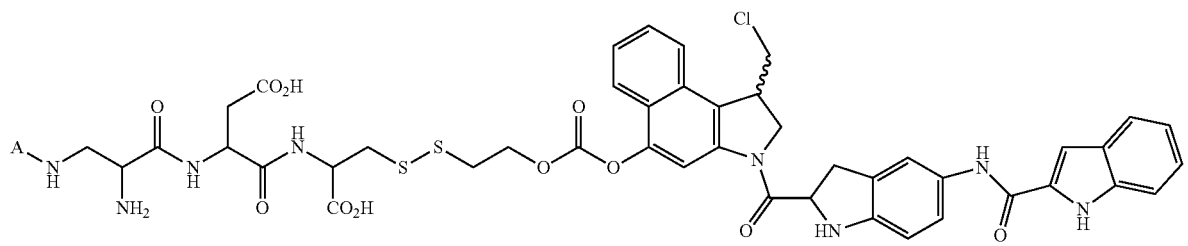
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.
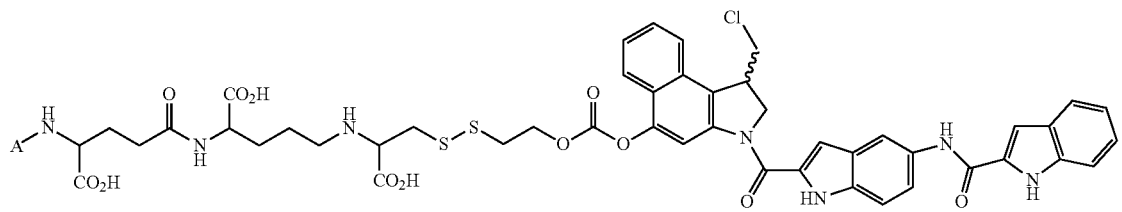
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.

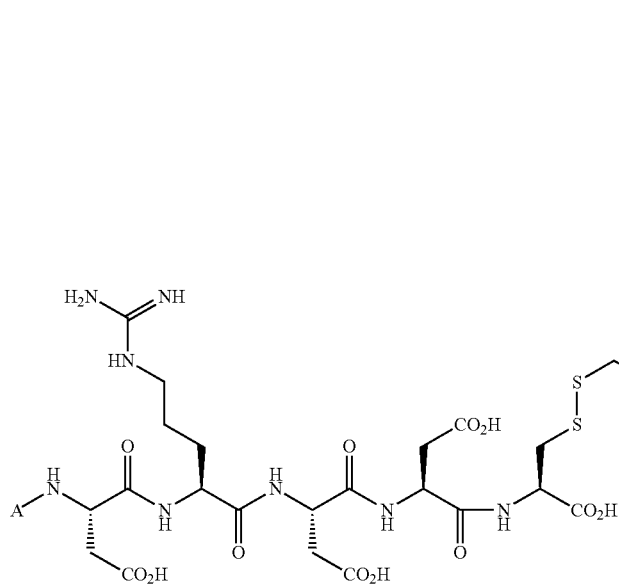
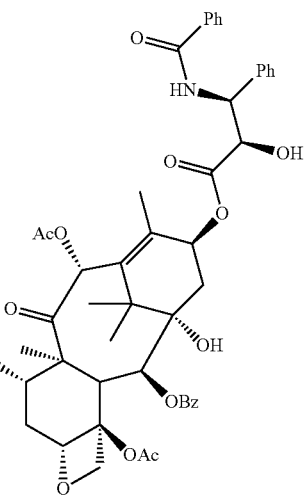
wherein A is N$^9$—CH$_3$-5-d(i)PteGlu, 5-d(i)PteGlu, IAHQ, BW1843U189, 2-NH$_2$-ZD1694, ZD1694, CB3717, 5-dH$_4$PteAPBA, 5-dPteHCysA, or DDATHF.
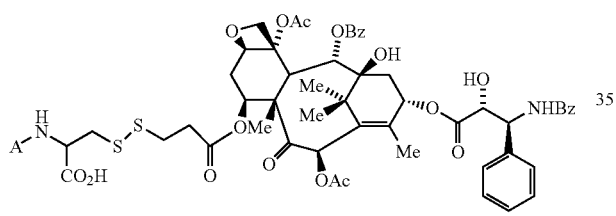
wherein A is N$^9$—CH$_3$-5-d(i)PteGlu, 5-d(i)PteGlu, IAHQ, BW1843U89, 2-NH$_2$-ZD1694, ZD1694, CB3717, 5-dH$_4$PteAPBA, 5-dPteHCysA, or DDATHF.
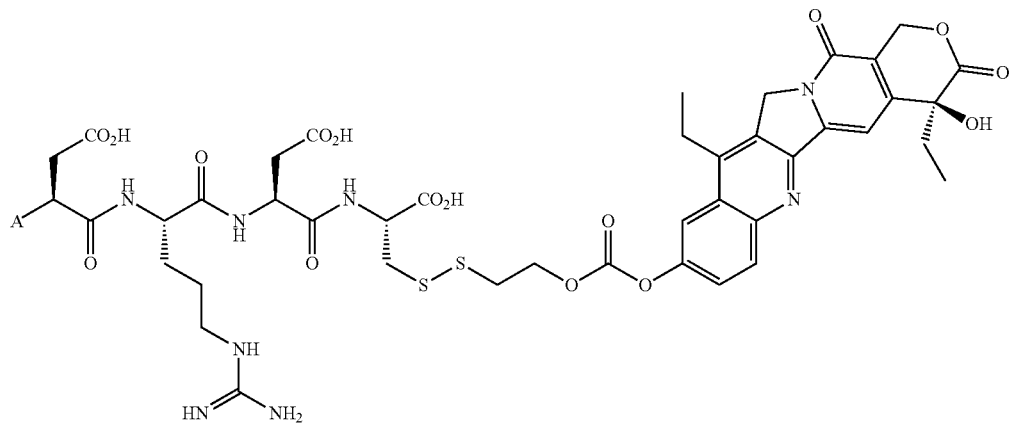
wherein A is N$^9$—CH$_3$-5-d(i)PteGlu, 5-d(i)PteGlu, IAHQ, BW1843U89, 2-NH$_2$-ZD1694, ZD1694, CB3717, 5-dH$_4$PteAPBA, 5-dPteHCysA, or DDATHF.

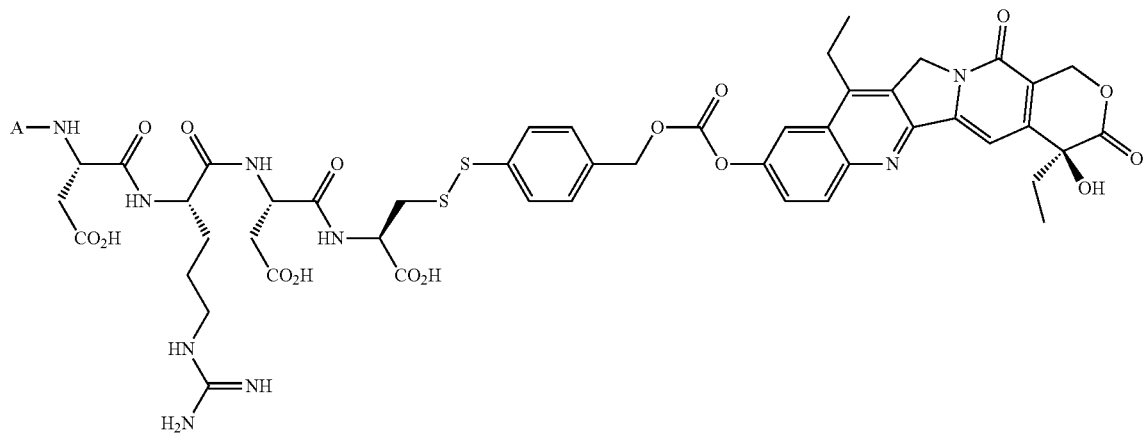
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.
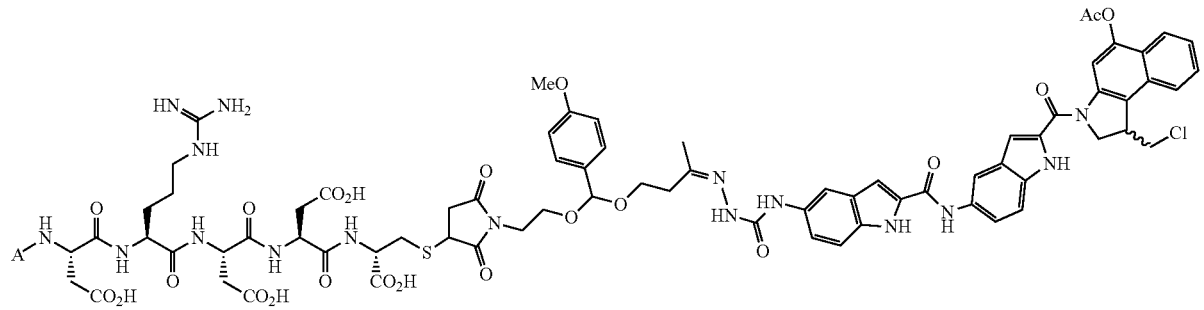
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.
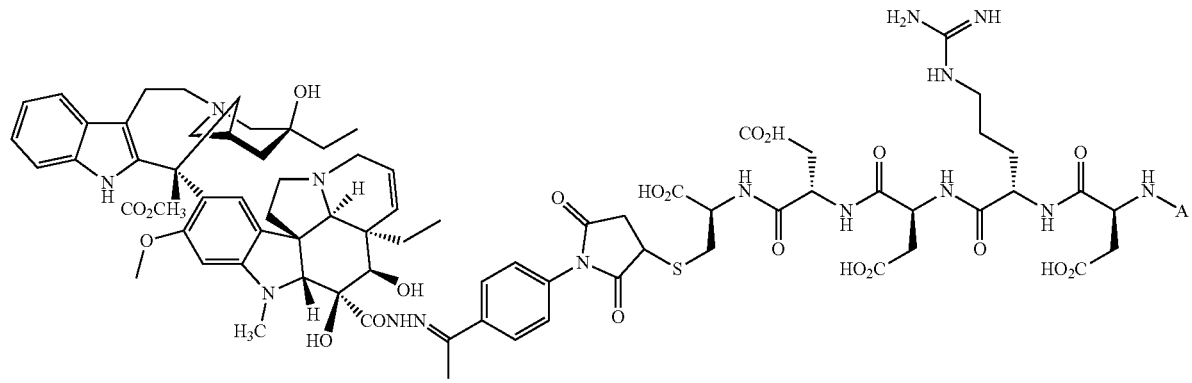
wherein A is $N^9$—$CH_3$-5-d(i)PteGlu, 5-d(i)PteGlu, IAHQ, BW1843U89, 2-$NH_2$-ZD1694, ZD1694, CB3717, 5-$dH_4$PteAPBA, 5-dPteHCysA, or DDATHF.

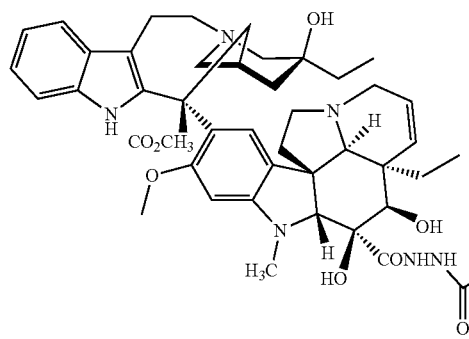
wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.
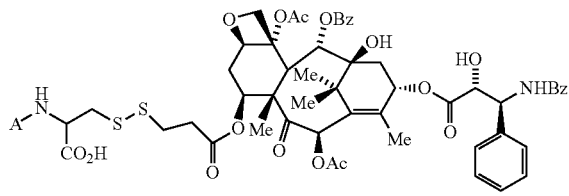
wherein A is N⁹CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.
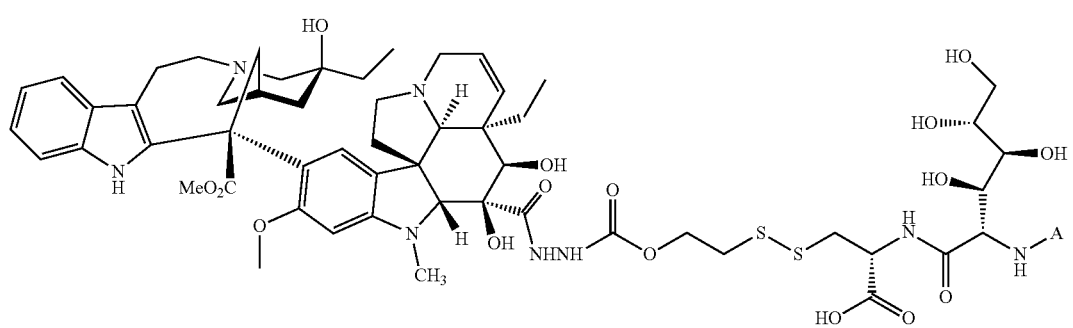
wherein A is N⁹—CH-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.
wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.

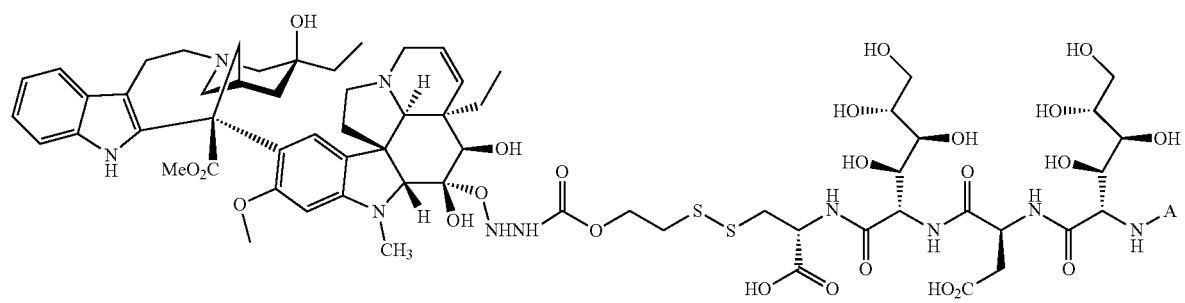
wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.
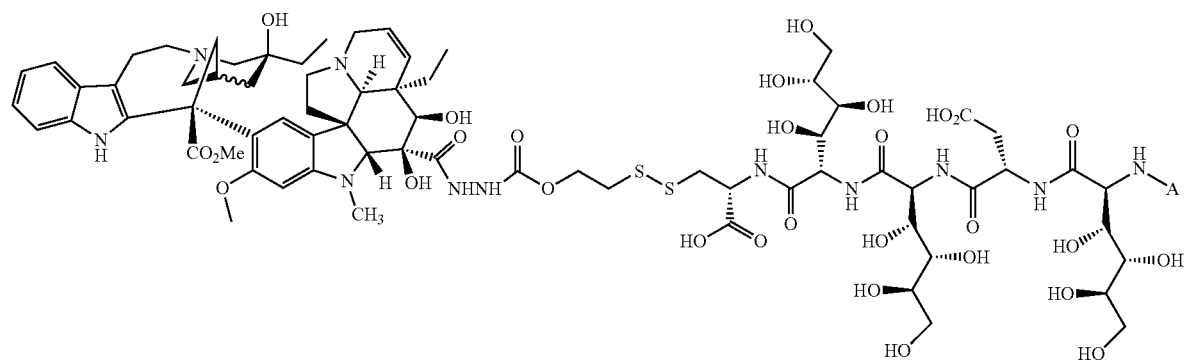
wherein A is N⁹—CH₃-5-d(i)PteGlu, 5-d(i)PteGlu, IAHQ, BW1843U89, 2-NH₂-ZD1694, ZD1694, CR3717, 5-dH₄PteAPBA, 5-dPteHCysA, or DDATHF.
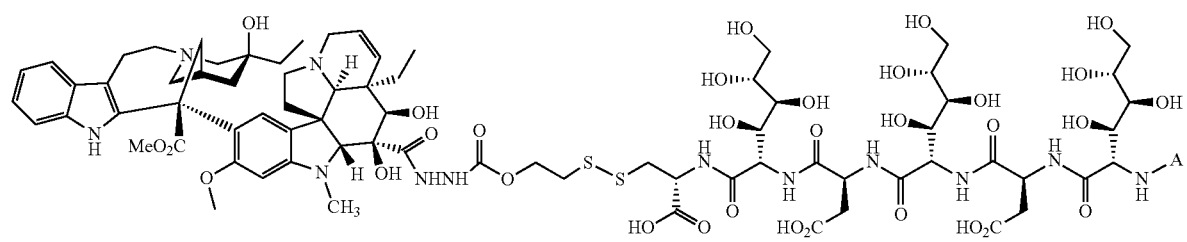
wherein A is N⁹—CH₃-5-d(i)PteGlu, 5-d(i)PteGlu, IAHQ, BW1843U89, 2-NH₂-ZD1694, ZD1694, CR3717, 5-dH₄PteAPBA, 5-dPteHCysA, or DDATHF.
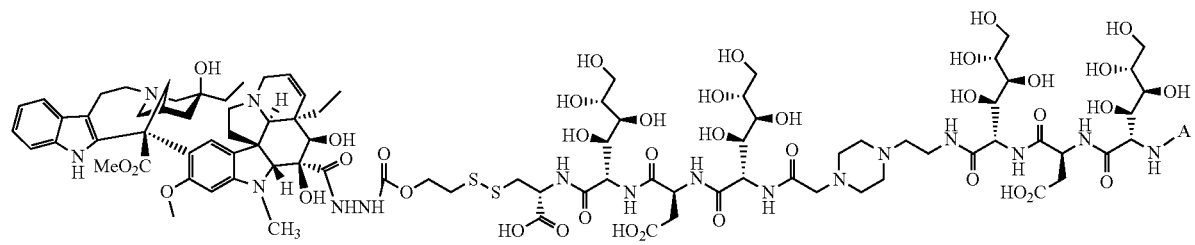

wherein A is N⁹—CH₃-5-d(i)PteGlu, 5-d(i)PteGlu, IAHQ, BW1843U89, 2-NH₂-ZD1694, ZD1694, CR3717, 5-dH₄PteAPBA, 5-dPteHCysA, or DDATHF.

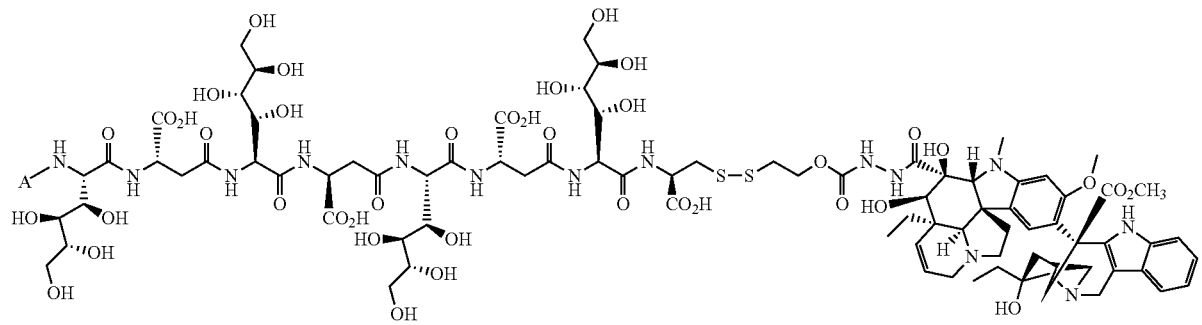

wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.

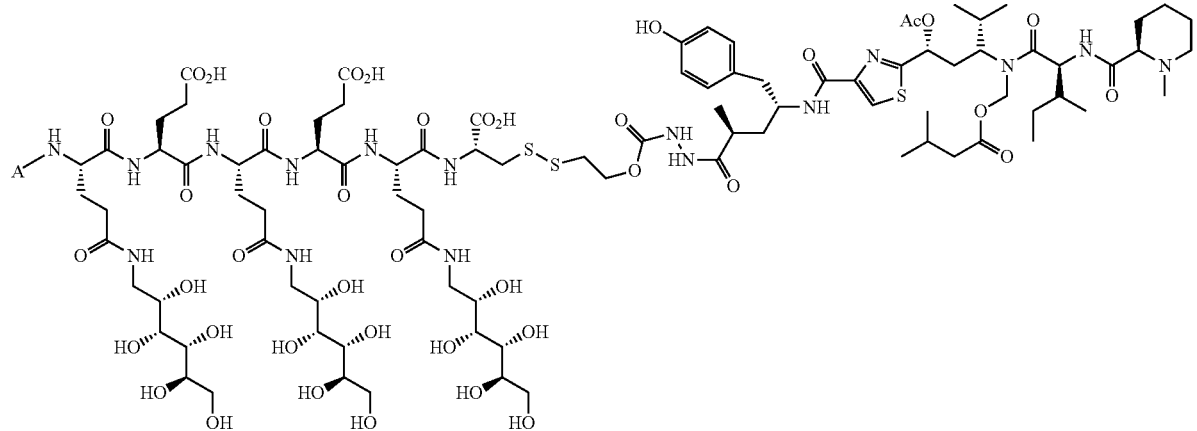

wherein A is N⁹—CH₃-5-d(i)PteGlu, 5-d(i)PteGlu, IAHQ, BW1843U89, 2-NH₂-ZD1694, ZD1694, CB3717, 5-dH₄PteAPBA, 5-dPteHCysA, or DDATHF.

It is understood that in the case of conjugates prepared from antifolate moieties that do not terminate in an acid function (e.g. 5-dH4PteOm), conjugates may be prepared by adding an intervening linker group. The intervening linker group is selected to contain functional groups that are capable of forming covalent bonds to the antifolate moiety and the bivalent linker moiety.

Method Examples

Cell culture. Cells were grown continuously as a monolayer using folate-free RPMI medium (FFRPMI) containing 10% heat-inactivated fetal calf serum (HIFCS) at 37° C. in a 5% CO₂/95% air-humidified atmosphere with no antibiotics. The HIFCS contained its normal complement of endogenous folates which enabled the cells to sustain growth in this more physiologically-relevant medium (Leamon et al. Proc Natl Acad Sci, USA 1991; 88:5572-6). All cell experiments were performed using FFRPMI containing 10% HIFCS (FFRPMI/HIFCS) as the growth medium unless otherwise specified.

Plate-Based Relative Affinity Assay. One hundred microliters of a FBP solution (10 μg/mL in PBS) were added to each well of a Reacti-Bind® microtiter plate. Plates were incubated at 4° C. overnight and then washed 3 times with cold PBS containing 0.05% Tween-20 (PBS-T). Plates were equilibrated to room temperature, blocked for 1 h on ice with 100 μL/well of freshly-prepared PBS-T containing 0.2% gelatin, and then washed 3 additional times with PBS-T. PBS solutions (100 μL per well) containing 100 nM of ³H-FA in the absence and presence of increasing concentrations of unlabeled FA or EC145 were added to designated wells in triplicate. Plates were incubated at 37° C. for 1 h with gentle shaking and then rinsed three times with PBS-T. Wells were stripped with 100 μL of acid-saline solution (20 mM sodium acetate, pH 3.0) for up to 20 in at room temperature, and the acidic samples were transferred into individual scintillation vials containing 3 mL of cocktail. Wells exposed to only the 100 nM ³H-FA solution (no competitor) were designated as Negative Controls, whereas wells exposed to 100 nM ³H-FA plus 1 mM unlabeled FA served as Positive Controls; DPMs measured in the latter samples (representing non-specific binding of label) were subtracted from the DPM values from all samples. Relative affinities were defined as the inverse molar ratio of compound required to displace 50% of ³H-FA bound to FR on KB cells, and the relative affinity of FA for the FR was set to 1.

Cell-Based Relative Affinity Assay. The relative affinity of each test article was determined based on a method initially described by Westerhoff et al. Mol Pharm 1995; 48:459-71) with modifications. Briefly, FR-positive KB cells were seeded in 24-well Falcon plates and allowed to form adherent monolayers (>75% confluent) overnight in FFRPMI/HIFCS. Spent incubation media was replaced with FFRPMI supplemented with 10% HIFCS and containing 100 nM of $^3$H-FA in the absence and presence of increasing concentrations of unlabeled FA or EC145. Cells were incubated for 1 h on ice or in an incubator at 37° C. (as specified in the figure legends) and then rinsed 3 times with 0.5 mL of PBS. Five hundred microliters of 1% sodium dodecylsulfate in PBS were added to each well; after 5 min, cell lysates were collected, transferred to individual vials containing 5 mL of scintillation cocktail, and then counted for radioactivity. Cells exposed to only the $^3$H-FA in FFRPMI (no competitor) were designated as Negative Controls, whereas cells exposed to the $^3$H-FA plus 1 mM unlabeled folic acid served as Positive Controls; DPMs measured in the latter samples (representing non-specific binding of label) were subtracted from the DPM values from all samples. Relative affinities were defined as described above.

Relative Affinity Assay Format. The in vitro RA assay described within measures a ligand's ability to compete with FA for binding to FRs. To date, cultured cells have most commonly been used as the FR source. However, herein described is the evaluation of the use of a cell-free, immobilized FR plate system for this assay. This latter method utilized a microtiter plate to which commercially-available bovine milk soluble FBP had been chemically anchored. Similar to the cell-based method, $^3$H-FA can compete directly with increasing concentrations of test article for binding to the attached FRs; however, unlike the cell-based method, bound radiolabel can be conveniently "stripped" from the plate by rinsing with a mildly acidic saline solution. For either assay, a relative affinity (RA) value of 1.0 implies that the test article ligand has an affinity equal to that of FA for the FR. Likewise, values lower than unity reflect weaker affinity, and values higher than unity reflect stronger affinity.

The functionalities of both the cell- and plate-based methods were directly compared using EC145, a folate conjugate of the microtubule destabilizing agent, desacetylvinblastine monohydrazide (DAVLBH; see Table 1). When evaluated under cold incubation conditions, EC145 was experimentally determined to have an RA of 0.19 relative to that of FA for human FRs (KB cells) and an RA of 0.12 for the plate-anchored bovine milk sFBP (see FIG. 1). Indeed, the results between the two assays are similar (less than a factor of 2). However, considering that (i) the KB cell assay involves the testing with the membrane-bound, human form of the FR, (ii) the plate-based assay uses bovine soluble folate binding protein, (iii) the plate assay is more expensive to conduct, and (iv) the cell-based assay requires less steps to complete, use of the cell-based assay was adopted for subsequent experiments.

Figure 2:
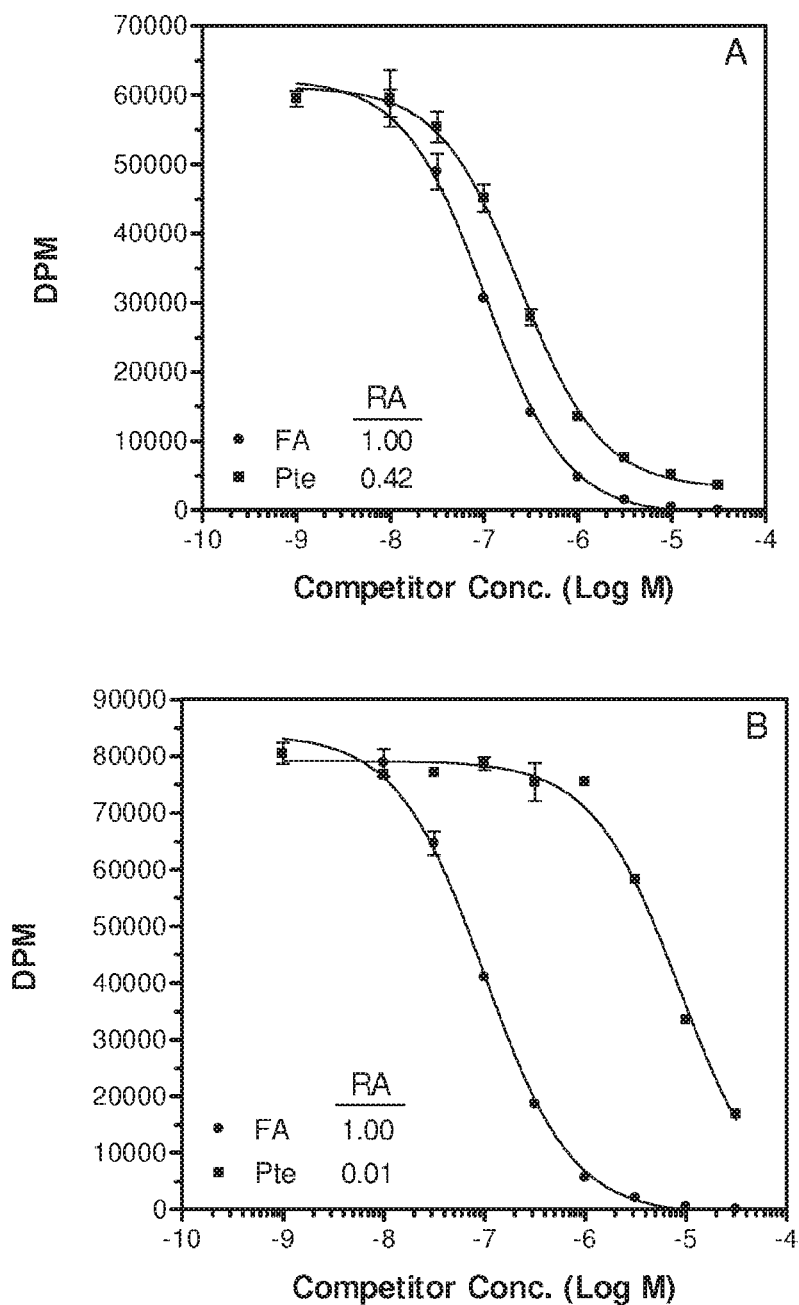
FIG. 2. Panel A, Pte acid on ice. Panel B, Pte at 37° C. Panel C, LV on ice. Panel D, LV at 37° C. Each assay was conducted using adherent KB cells as the FR source without serum in the test medium. FA=Pte-γGlu, (●); LV, (○); Pte (■).
Figure 2:
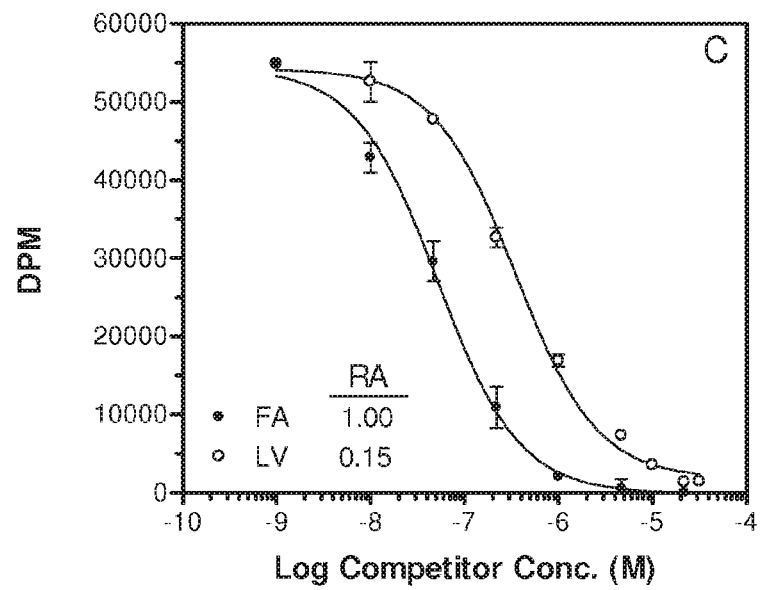
Figure 2:
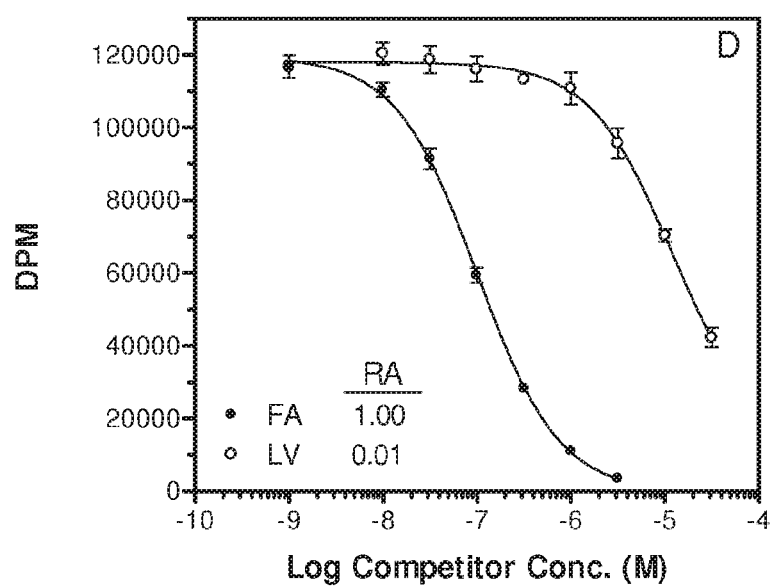
Figure 3:
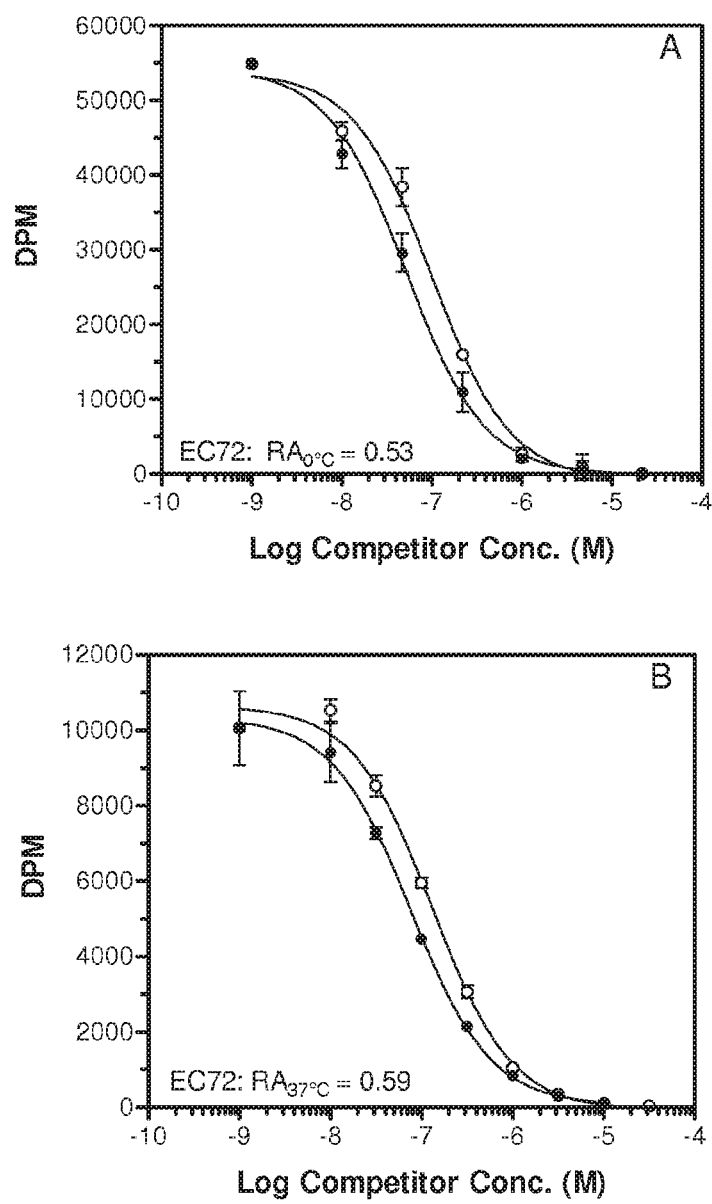
FIG. 3. Panel A, EC72 on ice. Panel B, EC72 at 37° C. Panel C, EC17 on ice. Panel D, EC17 at 37° C. Each assay was conducted using adherent KB cells as the FR source without serum in the test medium. FA, or Pte-γGlu, (●); EC72, (○); EC17 (■).
Figure 3:
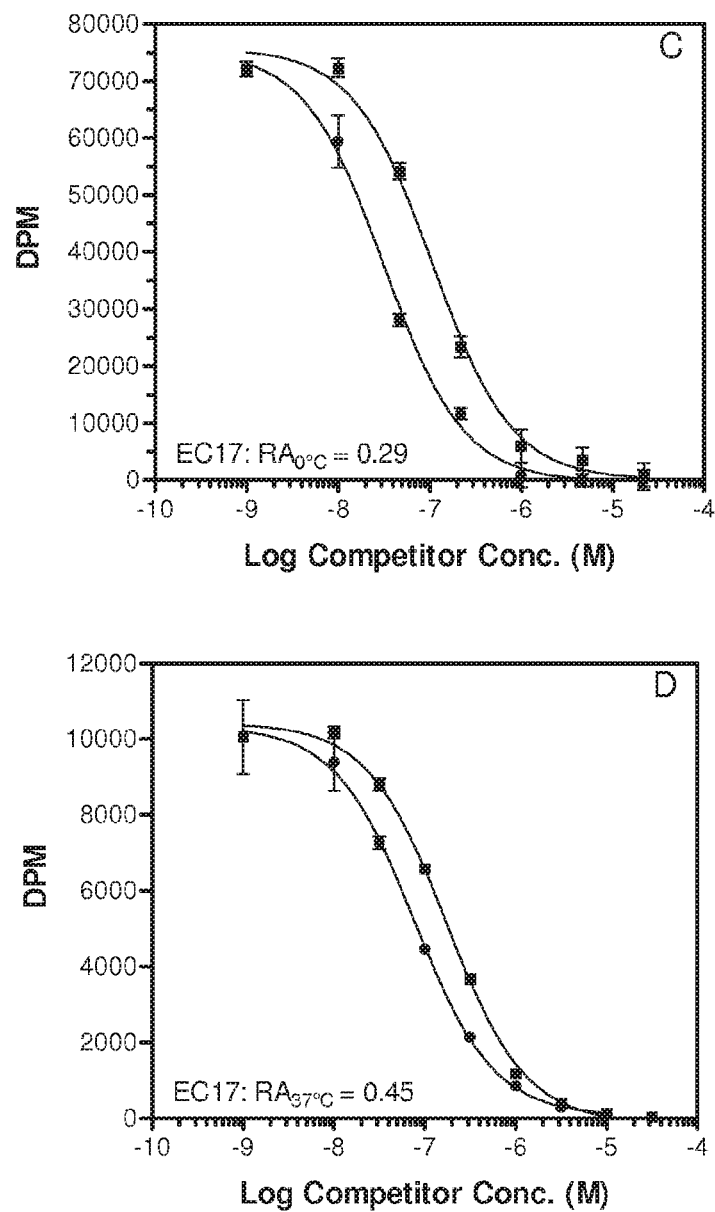

Temperature-Dependent Effects. The effect of incubation temperature on the relative affinities of a few related pteroates was measured. As shown in FIG. 2A, pteroic acid (Pte) was experimentally found to have an RA of 0.42, or an affinity 2.4-fold weaker than FA when tested using cells that were incubated on ice. This value was surprisingly high because other published reports had indicated that Pte displayed extremely low affinity for the FR (McHugh et al. J Biol Chem 1979; 254(22):11312-8; Kamen et al. Proc Natl Acad Sci, USA 1986; 83:5983-7). The source of discrepancy between these data and the historical data was investigated. Interestingly, upon repeating this assay at 37° C., the RA of Pte decreased dramatically to 0.01, or an affinity 100-fold weaker than FA. A similar pattern was also noted for leucovorin (LV; also called 5-formyltetrahydrofolate or folinic acid: see FIGS. 2C and D). Additional tests confirmed these findings (data not shown). Interestingly, such temperature-dependent effects were not always observed when a number of FA-drug conjugates were tested under similar conditions. In fact as shown in FIG. 3, the RAs of both EC72 (a mitomycin C conjugate of FA: and EC17 (a fluorescein conjugate of FA; increased with temperature. Subsequent tests were conducted at 37° C.

Figure 4:
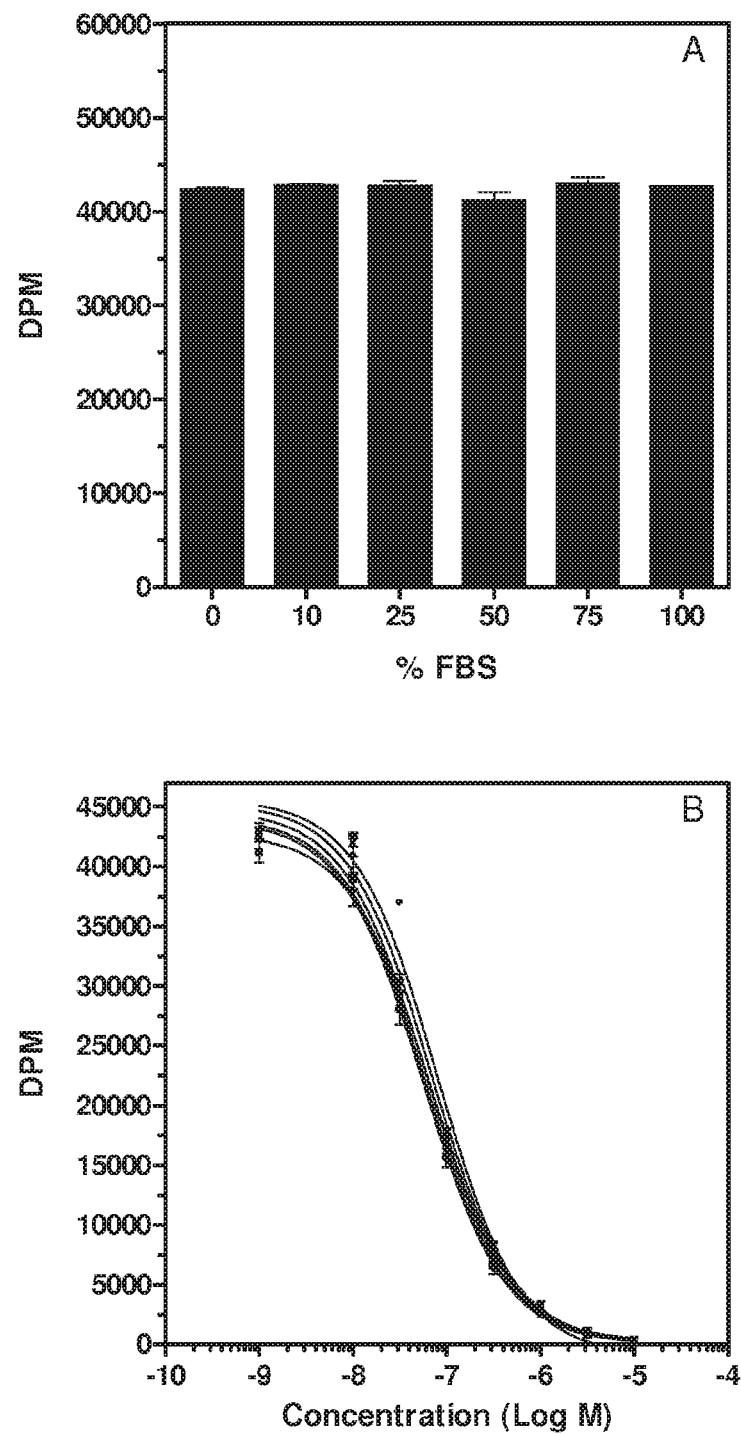
FIG. 4. Panel A, binding of FA to KB cells in the presence of increasing amounts of fetal bovine serum (FBS). Panels B and C, RA of FA and EC145, respectively (percent serum: 0% (●), 10% (■), 25% (▲), 50% (□), 75% (▽), 100% (○)). Panel D effect of 0% or 10% serum on the RA of EC140.
Figure 4:
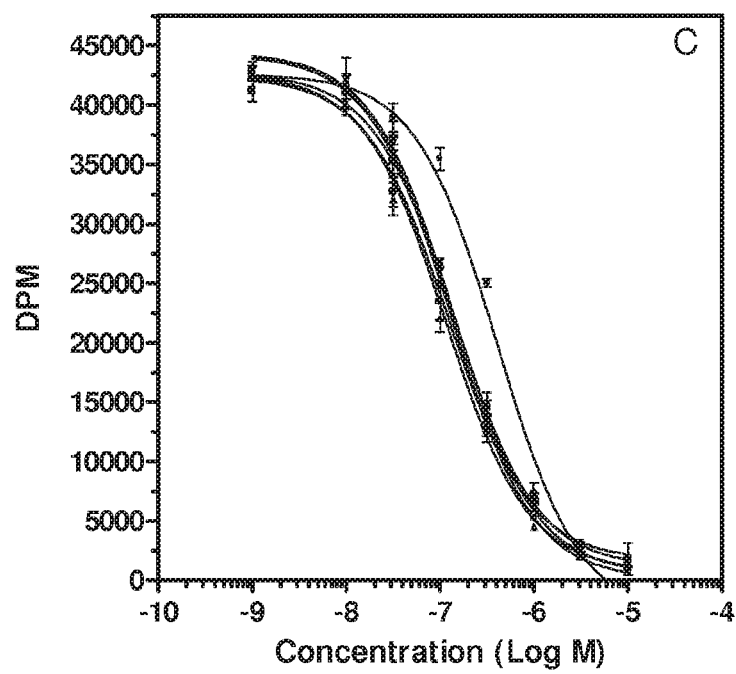
Figure 4:
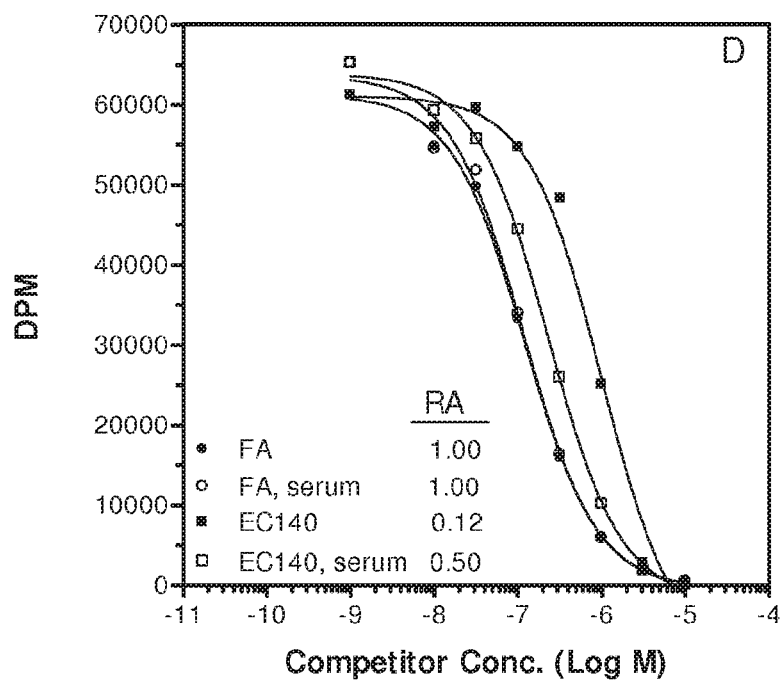

Serum-Dependent Effects. All of the aforementioned studies were conducted in the absence of serum. However, it is routine practice to evaluate the activity of folates, FA-drug conjugates, and even antifolates with cells in the presence of serum. To assess the impact that serum may have on the RA assay, the cell-associated binding level of $^3$H-FA was measured under conditions where the percent serum in the medium was varied. As shown in FIG. 4A, $^3$H-FA binding to KB cells was not found to be affected by fetal bovine serum, even when present at 100%. Likewise, increasing the percent sera from 0 to 100% had only a minor effect on unlabeled FA's ability to compete with $^3$H-FA for binding to KB cells (see FIG. 4B), the calculated RA values for FA varied by only 13% among all tested conditions. Interestingly, the RA value for the desacetylvinblastine monohydrazide FA conjugate, EC145, was found to remain nearly constant at 0.48 (±0.02) when sera was present at concentrations >10%; but, a 2.4-fold decrease in RA was reproducibly observed for EC145 when evaluated in the absence of serum (see FIG. 4C). To confirm this latter finding, the RA of a related Vinca alkaloid conjugate, EC140 (see structure in Table 1), was tested under similar conditions. As shown in FIG. 4D, the addition of 10% serum increased the RA of EC140 4-fold, from 0.12 (no serum) to 0.50. Notably, both EC145 and EC140 remain stable in 95% serum for incubation periods longer than 2 h (via HPLC-UV; data not shown): therefore, degradation and release of free FA from these conjugates is not responsible for these observations. Although the mechanism by which serum improves a FA-drug's RA is currently unknown, without being bound by theory, it is possible that dynamic interactions of the bulky drugs with serum proteins aids in the presentation of the FA moiety to the binding pocket of the FR. Test media including 10% fetal bovine serum were used in the standard conditions for all subsequent RA analyses.

Relative Affinity of Folate Analogs. Employing the defined assay conditions, which included the use of adherent KB cells as the FR source and a 10% serum-supplemented medium, a series of folate analogs were evaluated for their ability to compete for binding with % H-FA. As shown in Table 1, removal of the Glu residue in FA to produce Pte had caused a 91-fold reduction in RA (refer to FIG. 2B). Such results are consistent with other literature reports. Further removal of the p-aminobenzoyl moiety from Pte was found to completely eliminate competitive binding capability, since pterin-6-carboxylic acid failed to block $^3$H-FA's binding to KB cells at all concentrations evaluated. The most prevalent and natural serum-derived folate, 5-methyltetrahydrofolate (Antony et al. JBC 1985; 260(28):14911-7), and its 5-formyl counterpart, leucovorin, were found to display 14- and 125-fold weaker affinities for the FR, respectively; likewise, the popular anti-folate methotrexate (MTX) showed a 50-fold weaker affinity, CB3717, was found to have an RA value equal to that of FA. In contrast, the des-glutamyl analog had an RA value >300-fold lower (see Table 1). These data collectively suggest that a glutamyl moiety, or at least a hydrophilic moiety, positioned in close proximity to the p-aminobenzoyl (or aryl) group of the pteroate contribute to high binding affinity to the FR. Finally, it has been reported that that riboflavin binding protein and FR share ~27% homology. As measured by the assay described herein, riboflavin's RA to the KB-derived FR is very low. As shown in Table 1, even a 300-fold molar excess of this vitamin was not able to compete with the binding of $^3$H-FA to KB cells.

Influence of Drug on Relative Binding Affinity. The production of FA conjugates of drugs that are useful for applications in radiodiagnostic imaging, chemotherapy, immunotherapy and inflammation have been previously reported, as have the RA values for a few of those conjugates, including three clinical candidates. However, the assay conditions in those reports were not standardized. Described herein, in Table 2, are the RA values for some previously-reported conjugates as well as for many new ones that were all tested under standard assay conditions (namely, the use of adherent KB cells as the FR source, and a 10%-serum-supplemented 37° C. medium). The drugs in these conjugates widely varied from a metal-chelating peptide, to potent chemotherapeutics. However, for the most part the RA values all fell within a factor of ~2. Without being bound by theory, it is believed that this indicates that a flexible molecular spacer placed in-between the FA and drug moieties of the conjugates generally allows for efficient binding of the FA moiety to the FR. It has been found that a shorter spacer decreased the RA value for the desacetyl-vinblastine monohydrazide conjugate, EC216 (compare to EC145 in Table 2). However, it is appreciated that the spacer is not the only determinant that can affect a conjugate's RA, because a recently produced a steroid conjugate was found to have a 20-fold weaker binding affinity (EC0384; Table 2).

Figure 5:
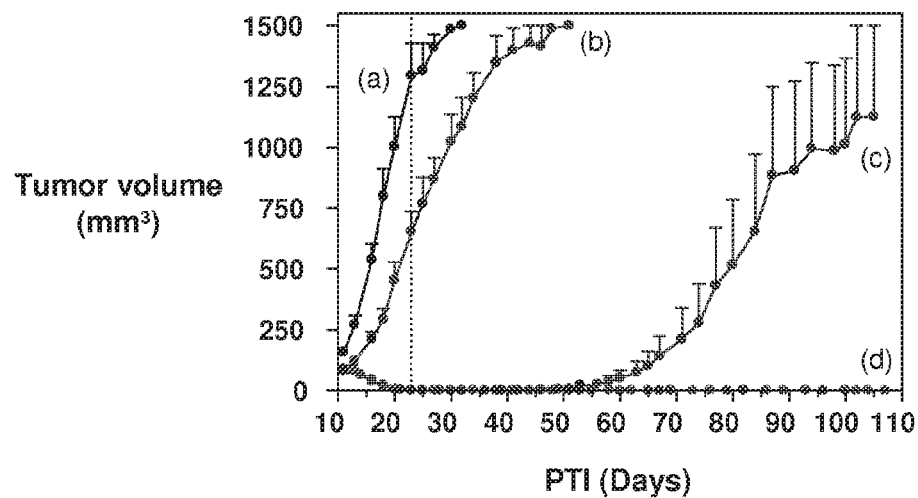
FIG. 5. Activity of compounds against subcutaneous KB tumors (2 μmol/kg TIW/2 weeks; vertical dotted line indicates last day of dosing): (a) Controls; (b) EC0282 (CB3717) 0/5 complete responses; (c) EC145 2/5 complete responses; (d) EC0284 5/5 complete responses.
Figure 6:
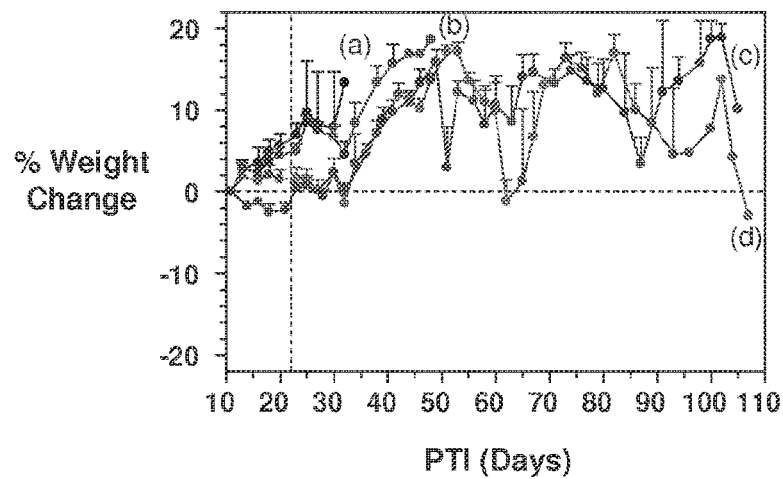
FIG. 6. Percent change in weight of treated animals in each test group. (2 μmol/kg TIW/2 weeks; vertical dotted line indicates last day of dosing): (a) Controls; (b) EC0282 (CB3717) 0/5 complete responses; (c) EC145 2/5 complete responses; (d) EC0284 5/5 complete responses.
Figure 7:
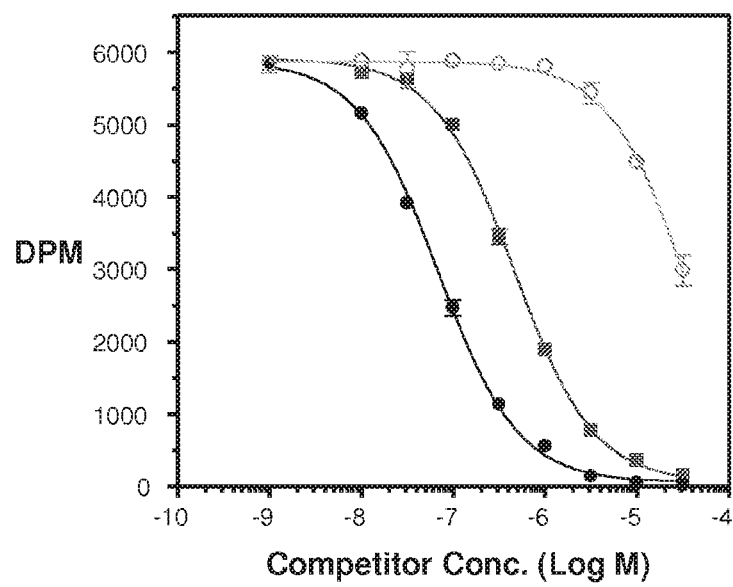
FIG. 7. Relative affinity assay (10% serum/FDRPMI): FA (●) 1.000; EC284 (■) 0.148; EC283 (○) 0.002.
Figure 8:
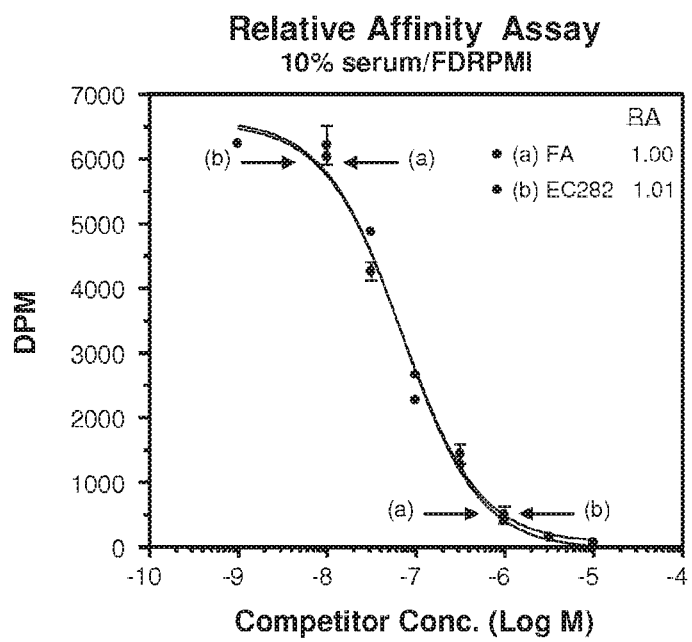
FIG. 8. Relative affinity assay (10% serum/FDRPMI): (a) FA (●) 1.000; (b) EC282 (●) 0.148
Figure 9:
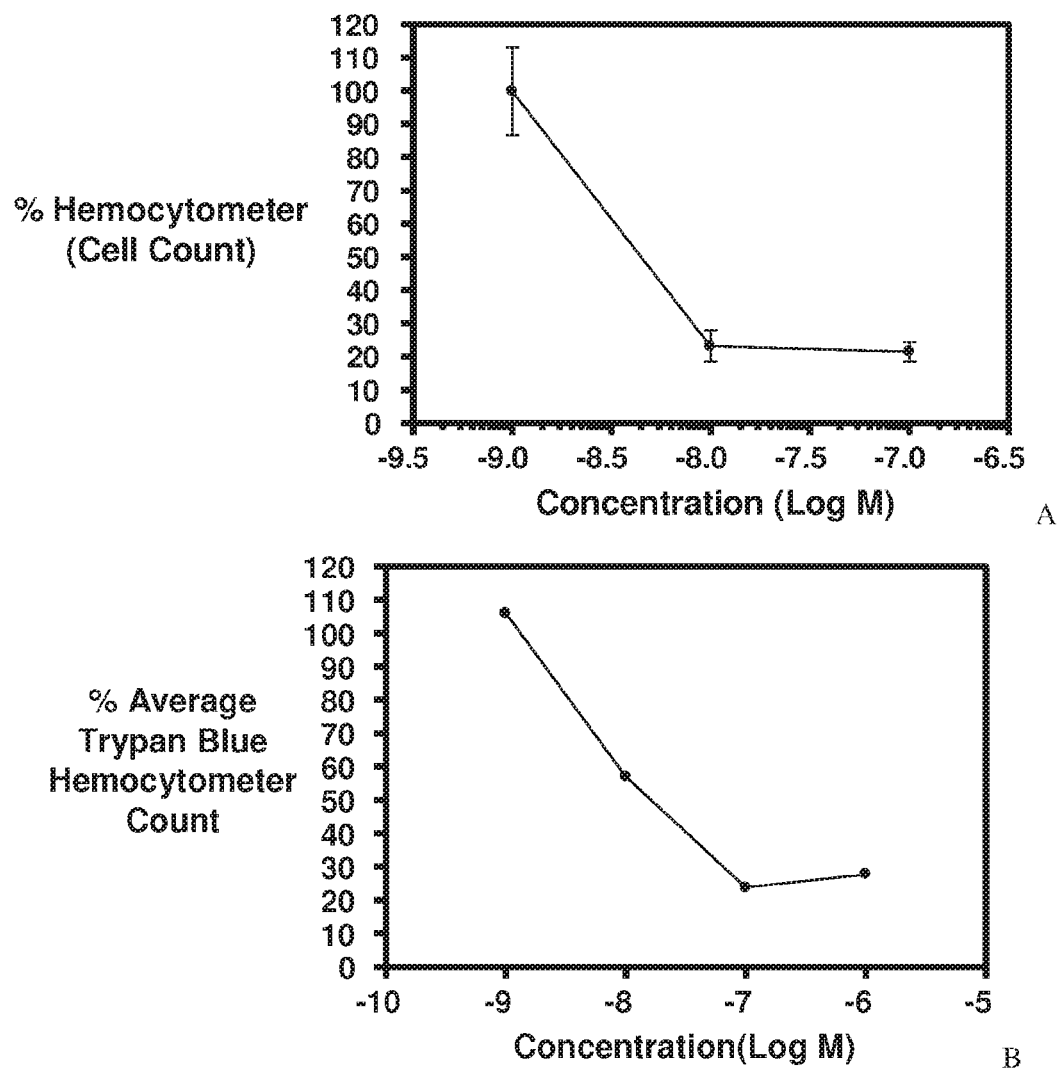
FIG. 9 Activity of EC282 against KB cells (72 h continuous Assay): Panel A. IC$_{50}$ 5 nM. Panel B. IC$_{50}$ 19 nM.
Figure 10:
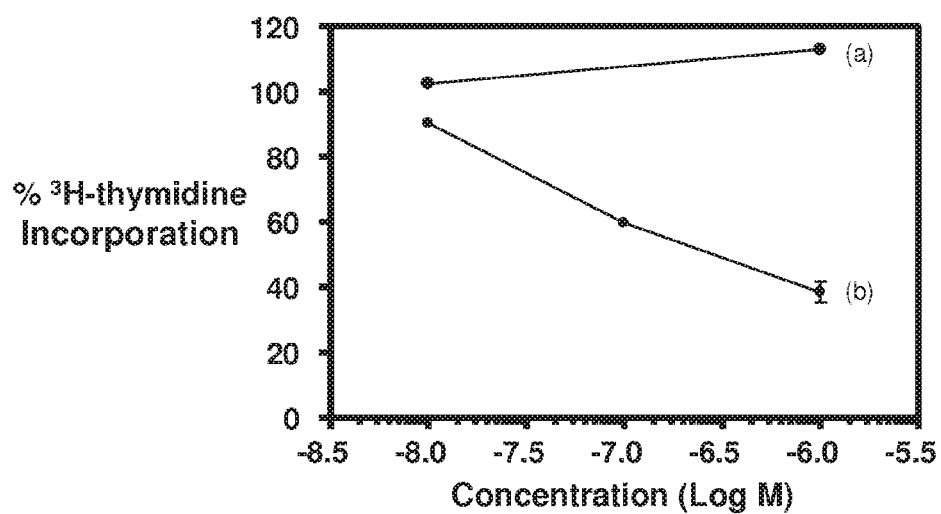
FIG. 10. Activity of EC0284 against KB cells (2 h treatment/72 h Assay): (a) EC0284+excess folic acid; (b) EC0284.

Effect On Transplanted KB Tumors. Mice are injected, subcutaneously with human KB tumor cells xenografts. Following a brief three times per week, 2-week schedule, animals appeared tumor-free (FIG. 5). The tumors did not regrow during the entire 110 day study The activity was not accompanied by any weight loss (FIG. 6), and it was competable with an excess of co-injected folates (an indicator of FR targeted specificity).

It is appreciated that conducting the binding affinity assays at lower temperature tends to increase the competitiveness of weaker affinity ligands. Accordingly, it is understood that the use of higher temperatures may be better to assess the relative binding affinity, as the resulting conditions may be more discriminating.

It is appreciated that the presence of serum in the test medium also proved to be important to the RA of FA-drug conjugates, but not to FA itself. For example, the RA values for both Vinca conjugates, EC145 and EC140, were shown to dramatically increase in the presence of serum (2.4- and 4.1-fold, respectively). These results could not be explained by degradation or release of FA from the conjugates because both agents were subsequently found to remain stable, even in 95% serum, for more than 2 h. Nonetheless, using a standardized protocol which included the use of adherent FR-positive KB cells exposed to 100 nM $^3$H-FA in the presence of increasing concentrations of competitor in 10% serum-supplemented medium at 37° C., a wide variety of folate analogs and FA-drug conjugates were screened and their RA values determined for comparison (see Tables 1 and 2).

It is further appreciated that among the folate analogs, it was interesting to observe the importance of having a charged moiety in close proximity to the Pte group. For example, the RA value increased 90 to >300-fold when a Glu residue was attached to Pte and $N^{10}$-propargyl 5,8-dideazapteroic acid, respectively. Notably, although a Glu residue is most often attached at this position, it is known that other amino acids can substitute for Glu without dramatically compromising binding affinity (Leamon et al. J Drug Targeting 1999; 7(3):157-69: McAlinden et al. Biochemistry 1991:30:5674-81; Westerhof et al. Proceedings of the American Association for Cancer Research 1991; 32:328). For the series of FA-drug conjugates examined, it was found that RA values remained within a factor of ~2 despite the wide structural variances present among the different drugs. But, two exceptions were found. The first showed that shortening the peptide-based spacer of EC145 from γGlu-Asp-Arg-Asp-Asp-Cys down to only a γGlu-Cys residue (in EC216) caused a 10-fold decrease in RA. It is appreciated that eliminating many of the charged groups in the spacer region may compromise the water solubility characteristics of the conjugate, but EC216 was observed to remain in solution (even at 30 μM) throughout the assay period. Therefore, without being bound by theory, it is believed that the lower RA value observed for FC216 may result from steric interference caused by the closer proximity of the drug (DAVLBH) to the Pte unit.

Another exception found was the 20-fold lower RA value which resulted when a lipophilic steroid had been linked to folate (EC0384; see Table 2). It was found that EC0384 binds serum protein with a value of >96%. The majority of folate conjugates bind serum protein with a value that is less than 80% (unpublished ob9331servations). Without being bound by theory, it is believed that this factor may, in part, explain the lower observed RA.

TABLE 1

Relative Affinity of Ligands at the Folate Receptor (cell assay).

| | Structure | Relative Binding Affinity (0° C.) | Relative Binding Affinity (37° C.) | Fold Weaker Affinity from FA |
|---|---|---|---|---|
| Folic Acid (Pte-Glu) | 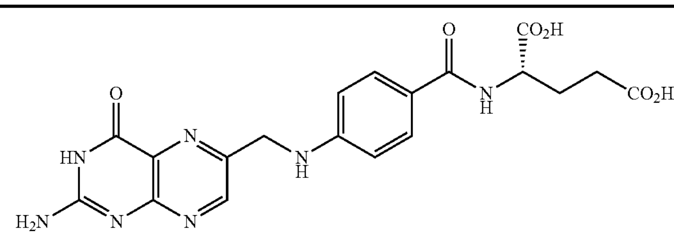 | — | 1,000 | 1.0 |

TABLE 1-continued

Relative Affinity of Ligands at the Folate Receptor (cell assay).

| Structure | Relative Binding Affinity (0° C.) | Relative Binding Affinity (37° C.) | Fold Weaker Affinity from FA |
|---|---|---|---|
| Pteroic Acid (Pte) | 0.42 | 0.011 | 91 |
| Pterin-6-carboxylate | — | 0.000 | n/a |
| 5-formyl-tetrahydrofolate (folinic acid, Leucovorin) | 0.15 (0.01)[a] | 0.008 | 125 |
| 5-methyl-tetrahydrofolate (5MTHF) | (0.35)[a] | 0.070 | 14 |
| Methotrexate (MTX) | 0.000 (0.008)[a] | 0.018 | 50 |
| CB3717 | — | 1.000 | 1.0 |

TABLE 1-continued

Relative Affinity of Ligands at the Folate Receptor (cell assay).

| | Structure | Relative Binding Affinity (0° C.) | Relative Binding Affinity (37° C.) | Fold Weaker Affinity from FA |
|---|---|---|---|---|
| Des-glutamyl CB3717 | 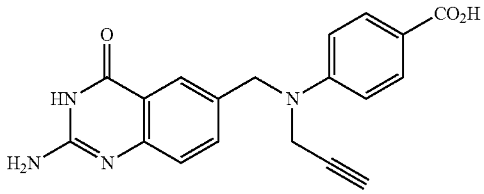 [SMILES: C#CCN(Cc1ccc2nc(N)[nH]c(=O)c2c1)c1ccc(C(=O)O)cc1] | — | 0.002 | 500 |
| Pemetrexed | 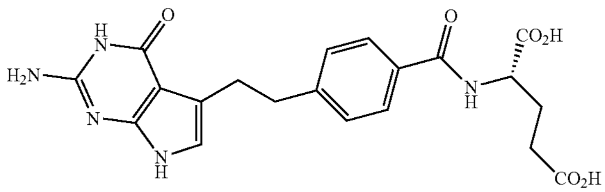 [SMILES: Nc1nc2[nH]cc(CCc3ccc(C(=O)N[C@@H](CCC(=O)O)C(=O)O)cc3)c2c(=O)[nH]1] | 0.26 (1.5)[a] | 0.002 | 500 |

[a] Westerhoff et al., Mol Pharm 48:459-71 (1995).

TABLE 2

Relative Affinity of Conjugates for the Folate Receptor (cell assay).

| Comparative Examples | Relative Binding Affinity (0° C.) | Relative Binding Affinity (37° C.) | Fold Weaker Affinity from FA |
|---|---|---|---|
| EC20 (Pte-γGluβDpr-Asp-Cys) | — | 0.92 | 1.1 |
| EC17 (Pte-γGlu-eda-FITC) | 0.29 | 0.45 | 1.2 |

TABLE 2-continued
Relative Affinity of Conjugates for the Folate Receptor (cell assay).
| Comparative Examples | Relative Binding Affinity (0° C.) | Relative Binding Affinity (37° C.) | Fold Weaker Affinity from FA |
|---|---|---|---|
| <br>EC72<br>(Pte-γGlu-Cys-L-MMC) | 0.53 | 0.59 | 1.5 |
| 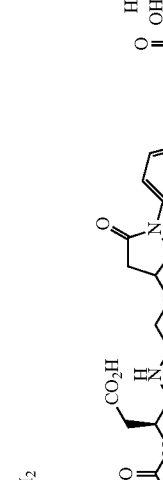<br>EC140<br>(EC119-Hyd-DAVLBH) | — | 0.50 | 2.0 |

TABLE 2-continued

Relative Affinity of Conjugates for the Folate Receptor (cell assay).

| Comparative Examples | Relative Binding Affinity (0° C.) | Relative Binding Affinity (37° C.) | Fold Weaker Affinity from FA |
|---|---|---|---|
| EC145 (EC119-L-DAVLBH) | — | 0.47 | 2.1 |
| EC216 (Pte-Cys-L-DAVLBH) | — | 0.046 | 22 |

TABLE 2-continued
Relative Affinity of Conjugates for the Folate Receptor (cell assay).
| Comparative Examples | Relative Binding Affinity (0° C.) | Relative Binding Affinity (37° C.) | Fold Weaker Affinity from FA |
|---|---|---|---|
| Antifolate Conjugate | | | |
| 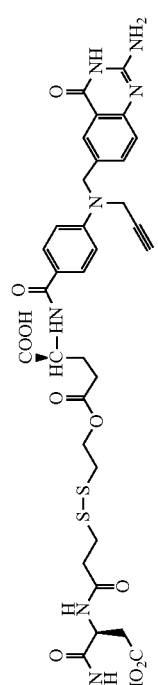 EC0284 | — | 0.15 | |

What is claimed is:
1. A conjugate of formula ALD$_m$, wherein
A is an antifolate of the formula:
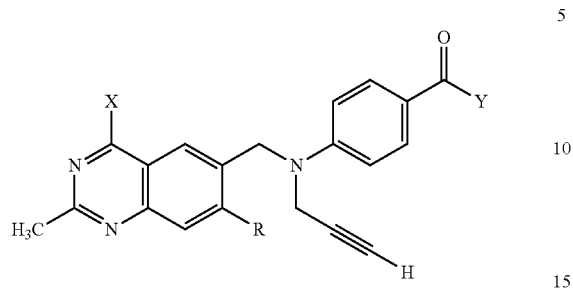
wherein
(1) X=OH, R=H, and Y=Glu; or
(2) X=OCH$_3$, R=H, and Y=Glu; or
(3) X=OH, R=H, and Y=Valine; or
(4) X=OH, R=H, and Y=Suberate; or
(5) X=OH, R=CH$_3$, and Y=Glu;
m is 1 to 3;
D is an independently selected drug; and
L is a linker comprising at least one releasable linker.
* * * * *

UNITED STATES PATENT AND TRADEMARK OFFICE
CERTIFICATE OF CORRECTION

PATENT NO. : 9,549,992 B2  
APPLICATION NO. : 14/919518  
DATED : January 24, 2017  
INVENTOR(S) : Christopher Paul Leamon, Iontcho Radoslavov Vlahov and Philip Steward Low Page 1 of 1

It is certified that error appears in the above-identified patent and that said Letters Patent is hereby corrected as shown below:

On the Title Page

After "Related U.S. Application Data", the paragraph labeled Item (63), is replaced with the following paragraph:

(63) Continuation of application No, 14/010,122, filed on Aug. 26, 2013, now Pat. No. 9,192,682, which is continuation of application No. 13/063,889, filed on Mar. 14, 2011, now Pat. No. 8,546,425, which is a National Stage Entry of application No. PCT/US2009/057363, filed on Sept. 17, 2009.

Signed and Sealed this  
Second Day of May, 2017

Michelle K. Lee  
*Director of the United States Patent and Trademark Office*